Figure 1:
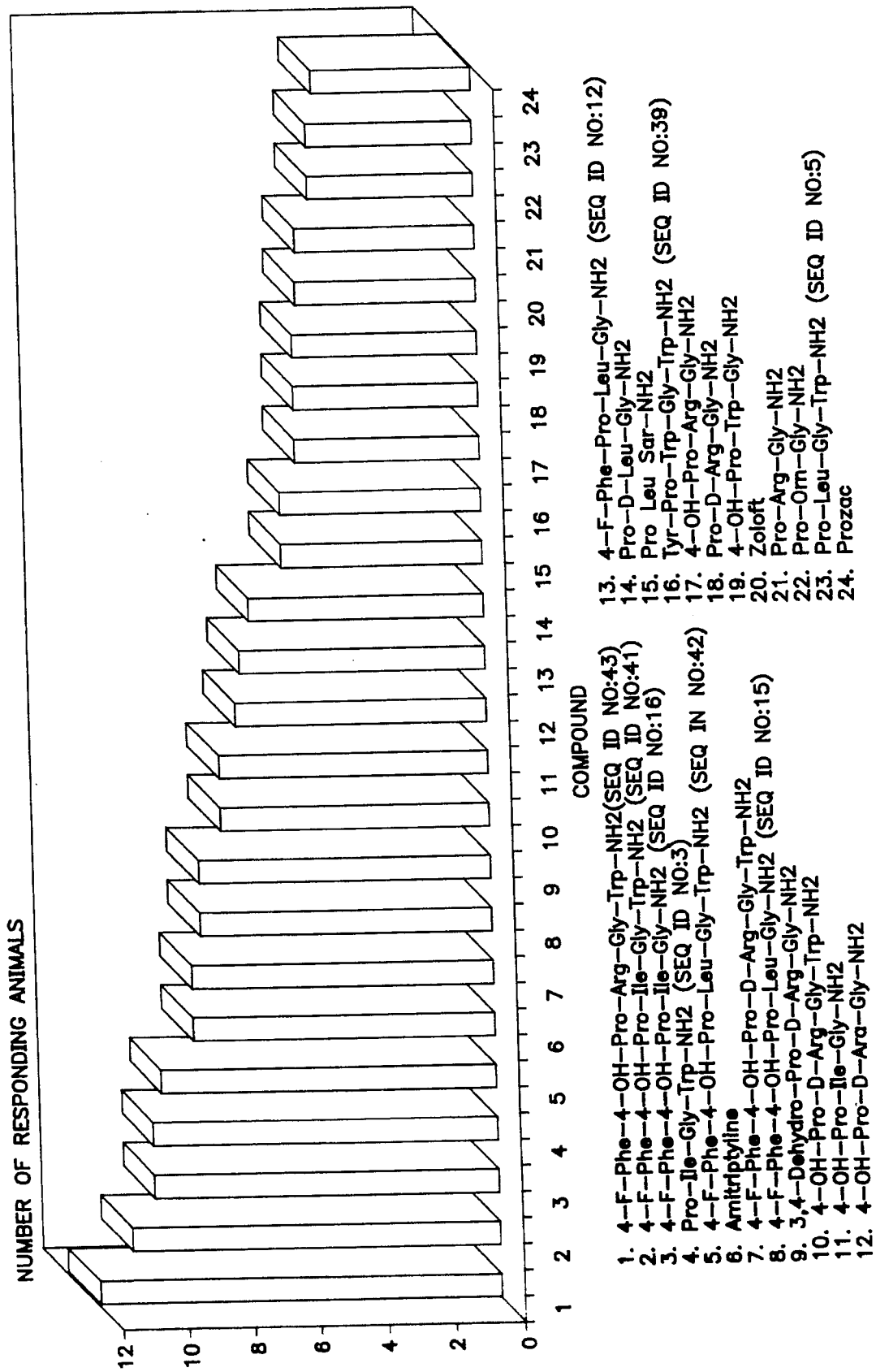

United States Patent [19]

Abajian et al.

[11] Patent Number: 5,589,460
[45] Date of Patent: Dec. 31, 1996

[54] TRI-, TETRA-, PENTA-, AND POLYPEPTIDES AND THEIR THERAPEUTIC USE AS AN ANTIDEPRESSANT AGENT

[75] Inventors: Henry B. Abajian, Hillsdale, N.J.; John F. Noble, Pomona; Joseph J. Hlavka, Tuxedo Park, both of N.Y.

[73] Assignee: Innapharma, Inc., Suffern, N.Y.

[21] Appl. No.: 238,089

[22] Filed: May 4, 1994

[51] Int. Cl.$^6$ .......................... A61K 38/04; A61K 38/07; C07K 5/04; C07K 7/06
[52] U.S. Cl. ................. 514/17; 514/16; 514/18; 514/19; 514/20; 530/329; 530/330; 530/331; 548/537
[58] Field of Search .................. 548/537; 530/331, 530/330, 329; 514/17, 18, 19, 20, 16

[56] References Cited

U.S. PATENT DOCUMENTS

| | | | |
|---|---|---|---|
| 3,708,593 | 1/1973 | Plotnikoff et al. | 514/2 |
| 3,795,738 | 3/1974 | Plotnikoff et al. | 514/19 |
| 3,821,188 | 6/1974 | McKinley et al. | 530/331 |
| 3,931,184 | 1/1976 | Lex | 530/331 |
| 4,018,912 | 4/1977 | Failli et al. | 514/18 |
| 4,278,595 | 7/1981 | Cort | 530/331 |
| 4,610,817 | 9/1986 | Albrecht et al. | 514/19 |

FOREIGN PATENT DOCUMENTS

| | | | |
|---|---|---|---|
| 108053 | 7/1982 | Japan | 530/331 |

OTHER PUBLICATIONS

FEBS Letters, vol. 37, No. 1, issued Nov. 1973, DesLauriers et al, "Intra-Molecular Motion In Peptides . . . ", pp. 27–32.
Heluetica, Chimica Acta, vol. 44, No. 14–15, issued 1961, Jaquenoud et al, "Synthese de la Ileu–oxytocine . . . ", pp. 113–122.
J. Am. Chem. Soc., vol. 82, issued 20 Mar. 1960, Studer et al, "Synthetic Work Related to Arginine–Vasopressin", pp. 1499–1501.
Int. J. Peptide Protein Res., vol. 10, issued 1977, Felix et al, "Synthesis, Biological Activity and Tritiation . . . ", pp. 299–310.
FEBS Letters, vol. 27, No. 2, issued Nov. 1972, Celis et al, "Structure–Activity Studies of MSH–Release–Inhibiting Hormone", pp. 327–330.
Coll. Czech. Chem. Comm., vol. 53, issued 1988, Reissmann et al, "Peptide Inhibitors of the Angiotensin . . . ", pp. 2591–2598.
Celis, et al., 1971, Regulation of Formation and Proposed Structure of the Factor Inhibiting the Release of Melanocyte–Stimulating Hormone, Proc. Natl. Acad. Sci. USA 68 (7): 1428–1433.
Nair, et al., 1971, Isolation Structure of Hypothalamic MSH Release–Inhibiting Hormone, Biochem Biophys. Research Commun., 43 (6): 1376–1381.
Hayashi, et al., 1984, Some Analogs of Tyr–MIF–1 Affect Passive Avoidance Behavior but not Motor Activity in Rats, Pharmacology Biochem & Behavior, 21:809–812.
Kastin, et al., 1984, Tyr–MIF–1 and MIF–1 are Active in the Water Wheel Test for Antidepressant Drugs, Pharmacology Biochem & Behavior, 21:767–771.
Kastin, et al., 1985, Tyr–MIF–1, Identified in Brain Tissue, and Its Analogs are Active in Two Models of Antinociception, Pharamacology Biochem & Behavior, 23:1045–1049.

(List continued on next page.)

*Primary Examiner*—Jeffrey E. Russel
*Attorney, Agent, or Firm*—Eckert Seamans Cherin & Mellott

[57] ABSTRACT

The present invention discloses novel peptides utilized to treat patients suffering from depression. These novel peptides are modifications of the tripeptide hormone MIF, including modification of amino terminus residues, carboxyl terminus residues and internal residues, including addition and substitution of amino acid residues and modification of the peptide bonds and functional side groups of respective amino acid residues. The tri-, tetra-, penta-, and polypeptides of the present invention may be utilized alone or in combination to treat patients suffering from depression.

68 Claims, 3 Drawing Sheets

OTHER PUBLICATIONS

Banks, et al., 1986, Carrier–Mediated Transport of Enkephalins and N–Tyr–MIF–1 Across Blood Brain Barrier, Am. J. Physiol. (Endorinol. Metab. 14): E477–E482.

Pulvirenti & Kastin, 1988, Blockade of Brain Dopamine Receptors Antagonizes the Anti–Immobility Effect of MIF–1 and Tyr–MIF–1 in Rats, European Journ. of Pharmacology, 151:289–292.

Hayashhi, et al., 1983, Tyr–MIF–1 Affects Passive Avoidance Behavior but not Motor Activity in Rats, Pharm Research Bulletin, 11:659–662.

TRI-, TETRA-, PENTA-, AND POLYPEPTIDES AND THEIR THERAPEUTIC USE AS AN ANTIDEPRESSANT AGENT

1. INTRODUCTION

Heterogeneous unipolar and bipolar depression is a common psychiatric disorder most likely mediated by neurochemical changes in the central nervous system. Administration of antidepressant drugs for treatment of unipolar depression has gained wide acceptance in the medical community over the past several decades. The present invention discloses novel peptides and their use as therapeutic agents in treating patients suffering from depression.

2. BACKGROUND OF THE INVENTION

Endogenous depression is thought to be a genetically determined biochemical disorder which results in an inability to deal with stress. This form of depression is oftentimes classified as unipolar depression, which is subclassified into retarded depression and agitated depression. Retarded depression is characterized by psychomotor retardation, where the subject does not interact with the surrounding environment to any extent. Agitated depression is, on the other hand, characterized by increased unproductive activity such as pacing, hand wringing, etc.

Unipolar depression is most likely a disorder resulting from a number of heterogeneous changes in the brain. One school of thought subscribes to the catecholamine theory: that endogenous depression is caused by a reduction in norepinephrine concentration within the vicinity of adrenergic receptor sites in the brain. Another possibility is that endogenous depression is caused by an absolute or relative deficiency in indoleamine, specifically 5-hydroxytryptamine, at receptor sites in the brain.

The course of treatment for endogenous depression is electroconvulsive therapy or drug therapy. The drugs administered for therapeutic treatment of depression include (1) tricyclic antidepressants, (2) monoamine oxidase (MAO) inhibitors, and (3) second-generation antidepressants.

Tricyclic drugs have been the drug of first choice in treating endogenous depression for over three decades. However, these drugs have limited efficacy in that two-thirds of patients receiving tricyclic drugs do not respond favorably. The side effects of the tricyclics are numerous, including cholinergic blockage, cardiac complications, allergic reactions, dry mouth, constipation, blurred vision and tachycardia. The tricyclic drugs are characterized structurally by a three-ringed nucleus. The tricyclic antidepressants include imipramine, desipramine, amitriptyline, nortriptyline, protriptyline, doxepin and trimipramine. These tricyclic structures are metabolized through the mixed-function oxidase system. These metabolites are the pharmacologically active compounds.

The MAO inhibitors have been available for treatment of depression since the 1950's. These compounds are classified either as hydrazides, exemplified by a C—N—N moiety (e.g., phenelzine and isocarboxazid) or a nonhydrazide (e.g., tranylcypromine). These drugs have not gained wide acceptance due to serious side effects.

The so called second-generation drugs are a group of new drugs which include amoxapine, maprotiline, fluoxetine, trazodone and bupropion. Most of these drugs seem to act in the same fashion as the tricyclic drugs.

Antidepressant drugs must cross the blood-brain barrier in pharmacologically effective concentrations. The capillaries of the central nervous system, unlike capillary beds feeding other organs, possess tight junctions with cerebral endothelial cells. Therefore, the human blood-brain barrier is a lipid barrier without pores. Any potential antidepressant drug must be designed such that the compound is able to traverse the blood-brain barrier. Compounds with low lipid solubility as well as many ionized compounds are unable to exit the circulation for entry into the extracellular fluid of the brain. Water soluble compounds will traverse the blood-brain barrier only if a specific membrane transport system exists. In contrast, lipid soluble drugs, in effect, are not hampered by the blood-brain barrier.

The tripeptide MIF, otherwise known as melanocyte stimulating inhibitory factor, which is represented by the chemical formula of prolyl-leucyl-glycinamide or Pro-Leu-Gly-$NH_2$, has been shown to produce numerous non-endocrine effects on the brain. The MIF tripeptide has also been shown to be active in a number of animal models for depression.

MIF was initially isolated and characterized from bovine hypothalmic extracts (Nair, et al., 1971, Biochem. Biohys. Res. Comm. 43(6): 1376–1381) and rat hypothalmic extracts (Celis, et al., 1971, Proc. Natl. Acad. Sci. USA 68(7): 1428–1433). MIF activity was attributed to inhibiting release of melanocyte stimulating hormone, a pituitary hormone known to stimulate melanin production. Neither disclosure suggests or discloses any potential antidepressant activity for MIF.

U.S. Pat. No. 3,708,593 (issued to N. P. Plotnikoff on Jan. 2, 1973) teaches that MIF exhibits antidepressant activity in mice, as shown by a modified Dopa test (Everett, et al., 1966, Proc. $1^{st}$ Int. Sym. Anti-depressant Drugs, p. 164).

U.S. Pat. No. 3,795,738 (issued to N. P. Plotnikoff on Mar. 5, 1974) teaches that MIF, alone or in combination with other known drugs, exhibits increased activity against Parkinson's disease.

U.S. Pat. No. 3,931,184 (issued to C. G. Lex on Jan. 6, 1976) teaches isolation of medicinally pure MIF. A MIF hemihydrate is dissolved in methanol, followed by the addition of diethyl ether, resulting in a white crystalline precipitate of MIF. This pure MIF is collected, washed with ether and dried under vacuum prior to use.

U.S. Pat. No. 4,278,595 (issued to J. H. Cort on Jul. 14, 1981) teaches that practical use of MIF has been hindered because MIF is rapidly metabolized subsequent to administration. Due to this relatively short half-lite of MIF, it has been necessary to administer large quantities of MIF intravenously over prolonged periods to obtain efficacious concentrations. Cort teaches a MIF analog characterized by replacement of Leu with its D-isomer, optionally replacing Pro with pGlu, and optionally alkylating the terminal amide group of Gly-$NH_2$ to produce a MIF analog. Such an analog may possess similar antidepressant activity as MIF and enhanced stability. Cort teaches a tripeptide having the formula X-D-Leu-$NH_2$—$CH_2$—$CONR^1R^2$, where X is Pro or pGlu and each of $R^1$ and $R^2$ independently is H or a lower alkyl, especially methyl or ethyl.

Tyr-MIF-1 (Tyr-Pro-Leu-Gly-$NH_2$) is a brain derived peptide shown to affect passive avoidance in rats (Hayashi, et al., 1983, Brain Res. Bull. 11: 659–662). Various analogs to Tyr-MIF-1 (i.e., substitutions for the Tyr residue, resulting in Ala-MIF-1, Leu-MIF-1 or Phe-MIF-1) were tested for a possible effect on behavioral and motor activities (Hayashi, et al., 1984, Pharmacology Biochemistry & Behavior 21:809–812). Ala-MIF-1 and Phe-MIF-1, but not Leu-MIF-1, affected passive avoidance behavior in rats. None of these peptides were shown to affect motor behavior.

Kastin, et al. (1984, Pharmacology Biochemistry & Behavior 21: 767–771) discloses that MIF-1 and Tyr-MIF-1 are active as antidepressants. The degree of activity was measured by the water wheel test, a modification of the Porolt swim test.

Kastin, et al. (1985, Pharmacology Biochemistry & Behavior 23: 1045–1049) determined that Tyr-MIF-1 and several Tyr-MIF-1 analogs possess antiopiate activity. Along with Tyr-MIF-1, Phe-MIF-1 was active in inhibiting the analgesic effect of morphine in rats.

Banks, et al. (1986, Am. J. Physiol. 251 [Endocrine Metabolism 14]: E477–E482) identifies the carrier-mediated transport system responsible for delivery of Tyr-MIF-1 to the extracellular brain fluid from the circulatory system.

It would be extremely useful to design and generate modified small peptides for treating patients suffering from depression which possess pharmacological activity subsequent to crossing the blood-brain barrier without inducing the side effects inherent in many of approved antidepressant drugs available today.

3. SUMMARY OF THE INVENTION

The present invention discloses modified small peptides for use as antidepressant compounds. According to the invention, these novel peptides are utilized to treat patients suffering from depression. These modifications target amino terminus residues, carboxyl terminus residues and internal residues, including addition and substitution of amino acid residues and modification of the peptide bonds and functional side groups of respective amino acid residues as more fully described hereinbelow.

It is an object of the invention to provide peptides which have pharmacologic activity.

It is another object of the invention to provide peptides useful in treating patients exhibiting symptoms of depression.

It is a feature of the invention to synthesize and provide small peptides representing novel modifications, substitutions, additions and/or deletions to a MIF core structure which have anti-depressant activity.

It is an advantage of the invention to provide small peptides which may be administered at lower dosages than known anti-depressants so as to reduce potential deleterious side effects.

In one embodiment of the invention, the small peptides of the present invention are tripeptides characterized by formula (1):

where $Pro^1$ represents the amino acid Pro or dehydro-Pro, preferably 3,4-dehydro Pro; $AA^1$ represents an amino acid of the group Trp, Orn, Lys, Leu, D-Leu, Arg, D-Arg, or Ile; R represents a carboxyl group, a hydroxyalkyl group, a carbamyl group, an alkylcarbamyl group, or an alkoxycarbonyl group; $R^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino group or dimethyl or diethylamino group; and, $R^2$ represents a hydrogen atom or a lower alkyl group, preferably having 1 to 3 carbon atoms, with the proviso that where $Pro^1$ is Pro and $AA^1$ is Leu, then $R^1$ and $R^2$ cannot both be a hydrogen atom when R is a carbamyl group, since MIF is a known compound.

An embodiment of tripeptides of formula (1) disclosed for utilization in treating depression in patients is formula (1a):

wherein $Pro^1$ and $AA^1$ are as described above for formula (1). Preferred compositions of the tripeptides of formula (1a) include, but are not necessarily limited to, Pro-Trp-Gly-$NH_2$, Pro-Arg-Gly-$NH_2$, Pro-D-Arg-Gly-$NH_2$, Pro-Lys-Gly-$NH_2$, Pro-Orn-Gly-$NH_2$, and Pro-Ile-Gly-$NH_2$.

Another embodiment of tripeptides of formula (1) disclosed for utilization in treating depression in patients is formula (1b):

wherein $Pro^1$, $AA^1$ and $R^1$ are as described above for formula (1). Preferred compositions of the tripeptides of formula (1b) include, but are not necessarily limited to cis- or trans-4-OH-Pro-D-Arg-Gly-$NH_2$, cis- or trans-4-OH-Pro-Ile-Gly-$NH_2$, cis- or trans-4-OH-Pro-Arg-Gly-$NH_2$, cis- or trans-4-OH-Pro-Trp-Gly-$NH_2$, and cis- or trans-4-thio-Pro-Leu-Gly-$NH_2$.

A further embodiment of tripeptides of formula (1) disclosed for utilization in treating depression in patients is formula (1c):

wherein $Pro^1$, $AA^1$, R and $R^2$ are as described above for formula (1), with the proviso that where $Pro^1$ is Pro and $AA^1$ is Leu, $R^2$ cannot be a hydrogen atom when R is either a carboxyl group or a hydroxyalkyl group, since these compounds, i.e., Pro-Leu-$NHCH_2$—$CO_2H$ (or Pro-Leu-Gly) and Pro-Leu-$NHCH_2$—$CH_2OH$, do not form part of this invention, and with the further proviso that where $Pro^1$ is Pro and $AA^1$ is Trp, $R^2$ cannot be a hydrogen atom when R is a hydroxyalkyl group, since Pro-Trp-$NHCH_2$—$CH_2OH$ is a known compound. Preferred compositions of the tripeptides of formula (1c) include, but are not necessarily limited to Pro-Leu-$N(CH_3)CH_2$—$CONH_2$ (or Pro-Leu-Sar-$NH_2$) and Pro-Trp-$NHCH_2$—$CO_2H$ (or Pro-Trp-Gly).

In yet a further embodiment, tripeptides of the present invention disclosed for utilization in treating depression in patients are represented by formula (2):

where $Pro^1$ represents the amino acid Pro or dehydro-Pro, preferably 3,4-dehydro Pro; $AA^1$ represents an amino acid of the group of Arg or D-Arg; R represents a carboxyl group, a hydroxyalkyl group, a carbamyl group, an alkylcarbamyl group, or an alkoxycarbonyl; and, $R^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of the tripeptides of formula (2) disclosed for utilization in treating depression in patients is disclosed in formula (2a):

wherein $Pro^1$ and $AA^1$ are as described above for formula (2). Preferred compositions of the tripeptides of formula (2a)

include, but are not necessarily limited to, Pro-Arg-Ala-NH$_2$ and Pro-D-Arg-Ala-NH$_2$.

In yet another embodiment, tripeptides of the present invention disclosed for utilization in treating depression in patients are represented by formula (3):

$$R^1\text{-Pro}^1\text{-AA}^1\text{-Tyr-R} \quad (3)$$

where Pro$^1$ represents the amino acid Pro or dehydro-Pro, preferably 3,4-dehydro Pro; AA$^1$ represents the amino acid Orn; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or a dimethyl or diethylamino group.

An embodiment of the tripeptides of formula (3) disclosed for utilization in treating depression in patients is formula (3a):

$$R^1\text{-Pro}^1\text{-AA}^1\text{-Tyr-NH}_2 \quad (3a)$$

where Pro$^1$, AA$^1$ and R$^1$ are as described for formula (3). Preferred compositions of the tripeptides of formula (3a) include, but are not necessarily limited to, Pro-Orn-Tyr-NH$_2$ and cis- or trans-4-OH-Pro-Orn-Tyr-NH$_2$.

The present invention also discloses tetrapeptides and use thereof in treating depression. One embodiment discloses C-terminus end enhanced tetrapeptide compositions represented by formula (4):

$$R^1\text{-Pro}^1\text{-AA}^1\text{Gly-AA}^2\text{-R} \quad (4)$$

where Pro$^1$ represents the amino acid Pro or dehydro-Pro, preferably 3,4-dehydro Pro; AA$^1$ represents Ile, Leu, Arg, D-Arg or Trp; AA$^2$ represents an amino acid of the group of Trp or Tyr; R represents a carboxyl group, hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of tetrapeptides of formula (4) disclosed for utilization in treating depression in patients is formula (4a):

$$R^1\text{-Pro}^1\text{-AA}^1\text{Gly-AA}^2\text{-NH}_2 \quad (4a)$$

wherein Pro$^1$, AA$^1$, AA$^2$, and R$^1$ are as described for formula (4). Preferred compositions of the tetrapeptides of formula (4a) include, but are not necessarily limited to, cis- or trans-4-OH-Pro-Leu-Gly-Trp-NH$_2$ (SEQ ID NO:1), cis- or trans-4OH-Pro-Ile-Gly-Trp-NH$_2$ (SEQ ID NO:2), cis- or trans-4-OH-Pro-D-Arg-Gly-Trp-NH$_2$, and 3,4-dehydro-Pro-D-Arg-Gly-Trp-NH$_2$.

A further embodiment of tetrapeptides of formula (4) disclosed for utilization in treating depression in patients is formula (4b) is:

$$\text{Pro}^1\text{-AA}^1\text{-Gly-AA}^2\text{-NH}_2 \quad (4b)$$

wherein Pro$^1$, AA$^1$ and AA$^2$ are as described for formula (4). Preferred compositions of the tetrapeptides of formula (4b) include, but are not necessarily limited to, Pro-Ile-Gly-Trp-NH$_2$ (SEQ ID NO:3), 3,4-dehydro-Pro-Ile-Gly-Trp-NH$_2$ (SEQ ID NO:4), Pro-Leu-Gly-Trp-NH$_2$ (SEQ ID NO: 5), Pro-Leu-Gly-Tyr-NH$_2$ (SEQ ID NO:6), Pro-Arg-Gly-Trp-Gly-Trp-NH$_2$ (SEQ ID NO:7), Pro-Trp-Gly-Trp-NH$_2$ (SEQ ID NO:8), Pro-D-Arg-Gly-Trp-NH$_2$, and Pro-Ile-Gly-Tyr-NH$_2$ (SEQ ID NO:9).

An additional embodiment of the tetrapeptides of the invention discloses N-terminus end enhanced tetrapeptide compositions represented by formula (5):

$$R^1\text{-AA}^1\text{-R}^2\text{-Pro}^1\text{-AA}^2\text{-Gly-R} \quad (5)$$

where Pro$^1$ represents the amino acid Pro or dehydro-Pro, preferably 3,4-dehydro Pro; AA$^1$ represents an amino acid of the group of Trp, Tyr or Phe; AA$^2$ represents an amino acid of the group of Leu, Ile, or Trp; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of tetrapeptides of formula (5) disclosed for utilization in treating depression in patients is formula (5a):

$$R^1\text{-AA}^1\text{-R}^2\text{-Pro}^1\text{-AA}^2\text{-Gly-NH}_2 \quad (5a)$$

wherein Pro$^1$, AA$^1$, AA$^2$, R$^1$ and R$^2$ are as described for formula (5), with the proviso that where Pro$^1$ is Pro, R$^1$ and R$^2$ cannot both be a hydrogen atom when AA$^1$ is Tyr and AA$^2$ is Trp, since this compound, i.e., Tyr-Pro-Trp-Gly-NH$_2$ (SEQ ID NO:54), is a known compound, and with the further proviso that where Pro$^1$ is Pro and AA$^2$ is Leu, R$^1$ and R$^2$ cannot both be a hydrogen atom when AA$^1$ is Phe or Tyr, since Phe-MIF-1 and Tyr-MIF-1 are known compounds. Preferred compositions of the tetrapeptides of formula (5a) include, but are not necessarily limited to, Trp-pro-Leu-Gly-NH$_2$ (SEQ ID NO: 10), 4F-Phe-Pro-Leu-Gly-NH$_2$ (SEQ ID NO:11), 4-F-Phe-Pro-Leu-Gly-NH$_2$ (SEQ ID NO: 12), 4-Cl-Phe-Pro-Leu-Gly-NH$_2$ (SEQ ID NO: 13), 4-F-Phe-Pro-Ile-Gly-NH$_2$ (SEQ ID NO: 14), 4-F-Phe-cis- or trans-4-OH-Pro-Leu-Gly-NH$_2$ (SEQ ID NO: 15), 4-F-Phe-cis- or trans-4-OH-Pro-Ile-Gly-NH$_2$ (SEQ ID NO: 16), Trp-Pro-Leu-Gly-NH$_2$ (SEQ ID NO: 17), Trp-Pro-Ile-Gly-NH$_2$ (SEQ ID NO: 18), Trp-cis- or trans-4-OH-Pro-Leu-Gly-NH$_2$ (SEQ ID NO: 19), and Trp-cis- or trans-4-OH-Pro-Ile-Gly-NH$_2$ (SEQ ID NO: 20).

The present invention further discloses pentapeptides and use thereof in treating depression. One embodiment of the pentapeptides according to the invention, discloses N-terminus enhanced pentapeptide compositions represented by formula (6):

$$R^1\text{-AA}^1\text{-AA}^2\text{-R}^2\text{-Pro}^1\text{-AA}^3\text{-Gly-R} \quad (6)$$

where Pro$^1$ represents the amino acid Pro or dehydro-Pro, preferably 3,4-dehydro Pro; AA$^1$ and AA$^2$ each independently represent an amino acid of the group of Phe or Tyr; AA$^3$ represents an amino acid of the group of Leu or Ile; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of the pentapeptides of formula (6) disclosed for utilization in treating depression in patients is formula (6a):

$$R^1\text{-}AA^1\text{-}AA^2\text{-}R^2\text{-}Pro^1\text{-}AA^3\text{-}Gly\text{-}NH_2 \quad (6a)$$

wherein Pro$^1$, AA$^1$, AA$^2$, R$^1$, and R$^2$ are as described of formula (6). Preferred compositions of the pentapeptides of formula (6a) include, but are not necessarily limited to, 4-F-Phe-Tyr-Pro-Leu-Gly-NH$_2$ (SEQ ID NO: 21), 4-Cl-Phe-Tyr-Pro-Leu-Gly-NH$_2$ (SEQ ID NO: 22), Phe-Tyr-Pro-Leu-Gly-NH$_2$ (SEQ ID NO: 23), Phe-Tyr-Pro-Ile-Gly-NH$_2$ (SEQ ID NO: 24), Phe-Tyr-cis- or trans-4-OH-Pro-Leu-Gly-NH$_2$ (SEQ ID NO: 25), Phe-Tyr-cis- or trans-4-OH-Pro-Ile-Gly-NH$_2$ (SEQ ID NO: 26), Tyr-Tyr-Pro-Leu-Gly-NH$_2$ (SEQ ID NO: 27), Tyr-Tyr-Pro-Ile-Gly-NH$_2$ (SEQ ID NO: 28), Tyr-Tyr-cis- or trans-4-OH-Pro-Leu-Gly-NH$_2$ (SEQ ID NO: 29), and Tyr-Tyr-cis- or trans-4-OH-Pro-Ile-Gly-NH$_2$ (SEQ ID NO: 30).

Another embodiment of the pentapeptides according to the invention, discloses combined N-terminus and C-terminus enhanced pentapeptide compositions represented by formula (7):

$$R^1\text{-}AA^1\text{-}R^2\text{-}Pro^1\text{-}AA^2\text{-}Gly\text{-}AA^3\text{-}R \quad (7)$$

where Pro$^1$ represents the amino acid Pro or dehydro-Pro, preferably 3,4-dehydro Pro; AA$^1$ represents an amino acid of the group of Phe or Tyr; AA$^2$ represents an amino acid of the group of Leu, Ile, Arg, D-Arg, or Trp; AA$^3$ represents the amino acid Trp; R represents a carboxyl group, hydroxyalkyl group, a carbamyl group, an alkylcarbamyl group, or an alkoxycarbonyl group; and, R$^1$ and R$^2$ each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

An embodiment of pentapeptides of formula (7) discloses for utilization in treating depression in patients is formula (7a):

$$R^1AA^1\text{-}R^2\text{-}Pro^1\text{-}AA^2\text{-}Gly\text{-}Trp\text{-}NH_2 \quad (7a)$$

wherein Pro$^1$, AA$^1$, AA$^2$, R$^1$ and R$^2$ are as described for formula (7). Preferred compositions of the pentapeptides of formula (7a) include, but are not necessarily limited to, Phe-Pro-Leu-Gly-Trp-N$_2$ (SEQ ID NO: 31), Tyr-Pro-Leu-Gly-Trp-NH$_2$ (SEQ ID NO: 32), Phe-cis- or trans-4-OH-Pro-Leu-Gly-Trp-NH$_2$ (SEQ ID NO: 33), Phe-Pro-Ile-Gly-Trp-NH$_2$ (SEQ ID NO: 34), Phe-cis- or trans-4-OH-Pro-Ile-Gly-Trp-NH$_2$ (SEQ ID NO: 35), Tyr-cis- or trans-4-OH-Pro-Leu-Gly-Trp-NH$_2$ (SEQ ID NO: 36), Tyr-Pro-Ile-Gly-Trp-NH$_2$ (SEQ ID NO: 37), Tyr-cis- or trans-4-OH-Pro-Leu-Gly-Trp-NH$_2$ (SEQ ID NO: 38), Tyr-Pro-Trp-Gly-Trp-NH$_2$ (SEQ ID NO: 39), Tyr-cis- or trans-4-OH-Pro-Trp-Gly-Trp-NH$_2$ (SEQ ID NO: 40), 4-F-Phe-cis- or trans-4-OH-Pro-Ile-Gly-Trp-NH$_2$ (SEQ ID NO: 41), 4-F-Phe-cis- or trans-4-OH-Pro-Leu-Gly-Trp-NH$_2$ (SEQ ID NO: 42), 4-F-Phe-cis- or trans-4-OH-Pro-Arg-Gly-Trp-NH$_2$ (SEQ ID NO: 43), and 4-F-Phe-cis- or trans-4-OH-Pro-D-Arg-Gly-Trp-NH$_2$.

Another embodiment of the pentapeptides according to the invention, discloses internal and C-terminus enhanced pentapeptide compositions represented by formula (8):

$$R^1\text{-}Pro^1\text{-}AA^1\text{-}AA^2\text{-}Gly\text{-}AA^3\text{-}R \quad (8)$$

where Pro$^1$ represents the amino acid Pro or dehydro-Pro, preferably 3,4-dehydro Pro; AA$^1$ and AA$^2$ each independently represent an amino acid of the group of Leu or Ile; AA$^3$ represents the amino acid Trp; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino group or dimethyl or diethylamino group.

An embodiment of pentapeptides of formula (8) disclosed for utilization in treating depression in patients is formula (8a):

$$R^1\text{-}Pro^1\text{-}AA^1\text{-}AA^2\text{-}Gly\text{-}Trp\text{-}NH_2 \quad (8a)$$

wherein Pro$^1$, AA$^1$, AA$^2$, and R$^1$ are as described for formula (8). Preferred compositions of the pentapeptides of formula (8a) include, but are not necessarily limited to, Pro-Ile-Leu-Gly-Trp-NH$_2$ (SEQ ID NO: 44) and cis- or trans-4-OH-Pro-Ile-Leu-Gly-Trp-NH$_2$ (SEQ ID NO: 45).

The present invention further discloses polypeptides of chemical combinations and/or overlapping chemical combinations of any of the peptides of formula (1) through formula (8) disclosed for utilization in treating depression in patients. These chemically combined polypeptides preferably have from at least about three to at least about ten modified and/or unmodified amino acids.

The small peptides of the present invention should be formulated in a suitable pharmaceutical carrier for in vivo administration to the patient by any standard method known in the art such that a pharmacologically effective concentration reaches the site of action. Appropriate routes of administration include, but are not limited to, oral (mouth or peroral administration), sublingual, parenteral (e.g., intravenous, intraspinal, intrathecal, intraventricular, epidermal, intracisternal, intracutaneous or intradermal, subcutaneous, or intramuscular), epicutaneous or transdermal, intranasal or rectal as well as inhalation (poly or mircodispersed aerosol).

3.1. DEFINITIONS

The terms listed below, as used herein, will have the meanings indicated.

PrO—L-proline;
Leu—L-leucine;
Gly—L-glycine;
Tyr—L-tyrosine;
Ala—L-alanine;
Arg—L-arginine;
Lys—L-lysine;
Phe—L-phenylalanine;
Trp—L-tryptophan;
Ile—L-isoleucine;
Orn—L-ornithine;
D-Arg—D-arginine;
D-Leu—D-leucine;
3,4-dehydro-Pro—3,4-dehydro-L-proline;
pGlu—pyro-glutamic acid;
Sar—L-sarcosine (N-methylglycine);
4-OH-Pro—4-hydroxyproline;
4-thio-Pro—4-thioproline;
4-F-Phe—4-fluorophenylalanine;
4-Cl-Phe—4-chlorophenylalanine;
Fmoc—9-Fluorenylmethoxycarbonyl;
TFA—trifluoroacetic acid;
carboxyl—carboxylic acid group or —CO$_2$H;

hydroxyalkyl—alcohol group or —ROH where R represents a lower alkyl group, preferably having 1 to 3 carbon atoms;

carbamyl—1° amide group or —CONH$_2$;

alkylcarbamyl—2° or 3° alkylated amide group or —CONR$^1$R$^2$ where R$^1$ and R$^2$ each independently represent a hydrogen atom, a lower alkyl group, preferably having 1 to 3 carbon atoms;

alkoxycarbonyl—ester group or —CO$_2$R where R represents a lower alkyl group, preferably having 1 to 3 carbon atoms dehydro—anhydro group where one or more hydrogen atoms are removed;

hydroxyl—alcohol group or —OH or —ROH where R represents a lower alkyl group, preferably having 1 to 3 carbon atoms;

sulphydryl—thiol group —SH or —RSH where R represents a lower alkyl group, preferably having 1 to 3 carbon atoms;

alkylamino——NHR where R represents a lower alkyl group, preferably having 1 to 3 carbon atoms;

dialkylamino——NR$_2$ where R represents a lower alkyl group, preferably having 1 to 3 carbon atoms;

patient—includes any member of the animal kingdom, including but not solely limited to humans; and, CGI—Control group inactive.

4. BRIEF DESCRIPTION OF THE FIGURES

Figure 2:
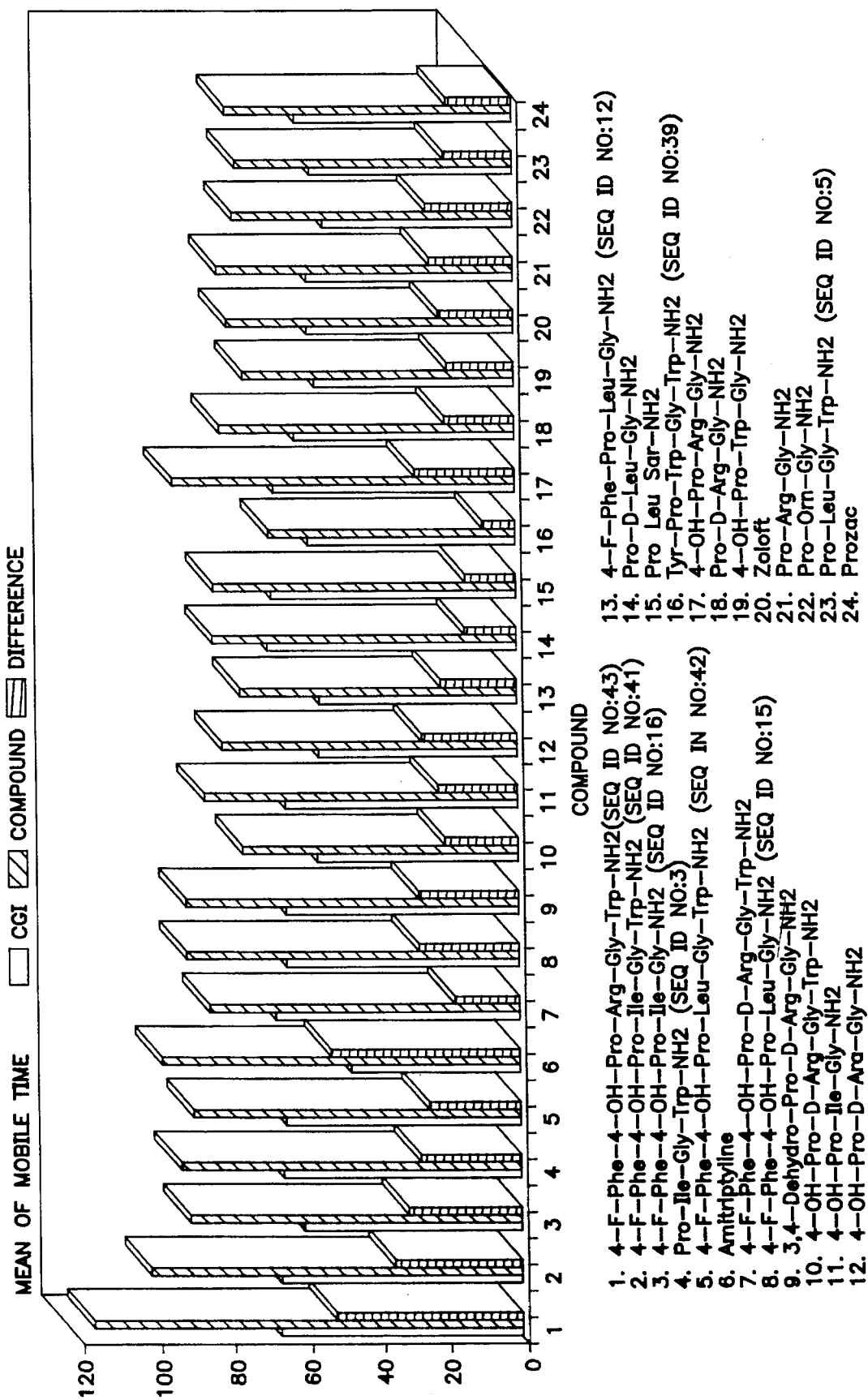
Figure 3:
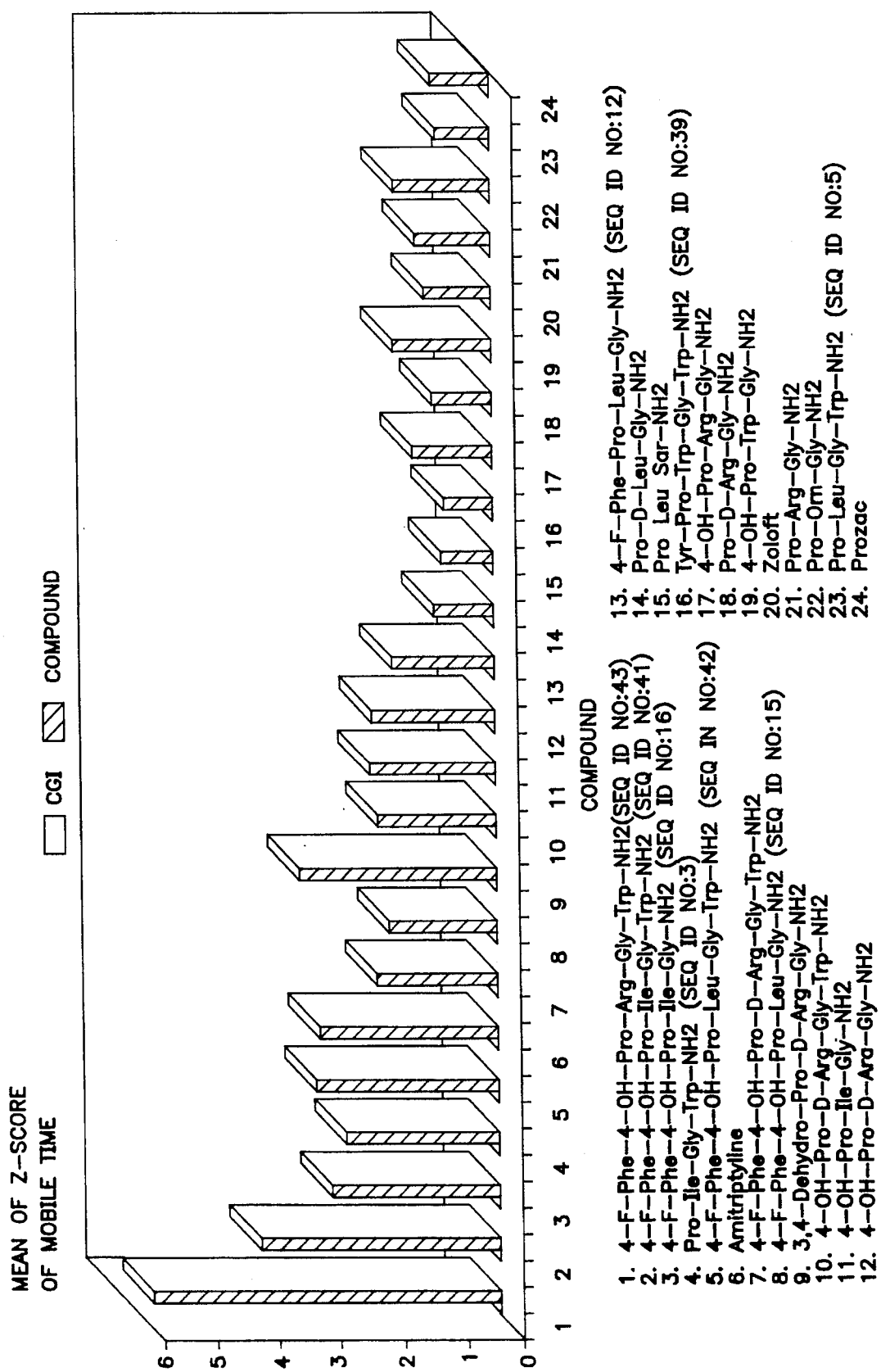

There are shown in the Figures certain exemplary small peptide compositions of the invention and pharmacological efficacy thereof as antidepressants as presently preferred. It should be understood that the invention is not limited to the embodiments disclosed as examples, and is capable of variation within the scope of the appended claims. In the drawings, FIG. 1 shows the average number of responding animals in the Porsolt swim test for compounds 1–24;

FIG. 2 shows the mean mobile time for difference between the CGI and compounds 1–24, respectively; and, FIG. 3 shows the mean of Z-score of calculated mobile time for compounds 1–24.

5. DETAILED DESCRIPTION OF THE INVENTION

The tripeptide hormone fragment having the general formula Pro-Leu-Gly-NH$_2$, otherwise known as L-prolyl L-leucyl glycine, melanocyte stimulating inhibitory factor, melanotrophic release inhibiting factor, or MIF, is known to exhibit antidepressant activity. MIF is typically reported in literature as having the tripeptide structure Pro-Leu-Gly-NH$_2$ or Pro-Leu-Gly-amide. MIF will be referred to herein as Pro-Leu-Gly-NH$_2$ having the following chemical structure:

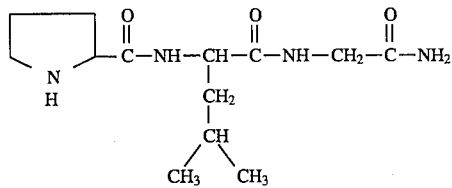

According to the invention, modifications of the tripeptide structure of MIF result in novel small peptides utilized to treat patients suffering from depression. These modifications target amino terminus residues, carboxyl terminus residues and internal residues, including addition and substitution of amino acid residues and modification of the peptide bonds and functional side groups of respective amino acid residues as more fully described hereinbelow.

In general, the amino acid(s) additions or substitutions at the amino terminus (N-terminus), carboxyl terminus (C-terminus), or internal amino acid residues to the MIF core sequence to synthesize the small peptides of the invention can be selected from the group of Ala, Arg, D-Arg, Gly, Ile, Leu, D-Leu, Lys, Orn, Phe, Pro, dehydro-Pro, Sar, Trp, and Tyr or any of the remaining amino acids. The carboxyl terminus modifications of the small peptides of the invention can include optional replacement of the carbamyl (amide) group at the carboxyl terminus of the MIF core sequence by a carboxyl (acid) group, a hydroxyalkyl (alcohol) group, an alkoxycarbonyl (ester) group, or an alkylcarbamyl (alkylated amide) group, and the like. The amino terminus and internal modifications of the small peptides of the invention can include optional additions or eliminations on the heterocyclic, aromatic, and other carbon residues of the amino acids with an alkyl group, preferably an alkyl group having 1 to 3 carbon atoms, a dehydro (anhydro) group, a halo group, a hydroxyl group, a sulphydryl group, an alkylamino group, or a dialkylamino group, and the like. Furthermore, the amino groups of the small peptides of the invention can be alkylated, preferably with an alkyl group having 1 to 3 carbon atoms. It should be understood by a person of ordinary skill that these additions, substitutions, eliminations, and/or modifications can be carried out by conventional polypeptide synthesis and organic chemistry synthesis techniques.

This specification details extensive biological data supporting the following premise: small peptides disclosed herein show substantial antidepressant activity as measured in the Porsolt swim test. The Example Section contains comparative data of exemplified peptides of the present invention and known antidepressants amitriptyline, fluoxetine (Prozac) and sertraline (Zoloft) generated in a series of Porsolt swim tests. The groupings of the small peptides of the invention into the formulas described below are provided only as a matter of convention and should not be considered limiting in any manner.

In one embodiment of the invention, the small peptides are tripeptides characterized either by optional replacement of the Leu residue of the MIF core sequence with an amino acid selected from the group of Trp, Orn, Lys, Arg, D-Arg, or Ile; optional replacement of the Pro residue with dehydro-Pro, preferably 3,4-dehydro-Pro; optional modification of the carboxyl terminus amide group with a substituent selected from a carboxyl group, an hydroxyalkyl group, preferably a hydroxymethyl group, an alkoxycarbonyl group, or an alkylated carbamyl group; optional modification of the amino terminus heterocyclic group or dehydro-heterocyclic group with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group; or an alkylamino group or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

This tripeptide composition or a pharmaceutically acceptable salt thereof can be represented by the following formula (1):

$$R^1\text{-}Pro^1\text{-}AA^1\text{-}NR^2\text{—}CH_2\text{—}R \tag{1}$$

where $Pro^1$ represents the amino acid Pro or dehydro-Pro, preferably 3,4-dehydro Pro; $AA^1$ represents an amino acid of the group of Trp, Orn, Lys, Leu, Arg, D-Arg, or Ile; R represents a carboxyl group, a hydroxyalkyl group, a carbamyl group, an alkylcarbamyl group, or an alkoxycarbonyl group; $R^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino group or dimethyl or diethylamino group; and, $R^2$ represents a hydrogen atom or a lower alkyl group, preferably having 1 to 3 carbon atoms, with the proviso that where $Pro^1$ is Pro and $AA^1$ is Leu, then $R^1$ and $R^2$ cannot both be hydrogen when R is a carbamyl (amide) group, since MIF is a known compound.

The following paragraphs discloses compositions of the tripeptides of formula (1), which may be utilized alone or in combination with other peptides disclosed in this specification to treat patients suffering from depression.

A first group of preferred compositions of the tripeptides of formula (1) which may be utilized alone or in combination with other peptides disclosed in this specification to treat patients suffering from depression are characterized by replacement of Leu, and are further characterized by having the N-terminus $Pro^1$ residue and C-terminus amide group remain unmodified, which can be represented by formula (1a). Formula (1a) is depicted as:

$$Pro^1\text{-}AA^1\text{-}Gly\text{-}NH_2 \tag{1a}$$

wherein $Pro^1$ and $AA^1$ are as described above for formula (1). The tripeptides of formula (1a), may be utilized alone or in combination with other peptides disclosed in this specification to treat patients suffering from depression. Preferred compositions of the tripeptides of formula (1a) are:

Pro-Trp-Gly-$NH_2$;

Pro-Arg-Gly-$NH_2$;

Pro-D-Arg-Gly-$NH_2$;

Pro-Lys-Gly-$NH_2$;

Pro-Orn-Gly-$NH_2$;

and,

Pro-Ile-Gly-$NH_2$.

A second group of preferred compositions of the tripeptides of formula (1) which may be utilized alone or in combination with other peptides disclosed in this specification to treat patients suffering from depression are characterized by optional replacement of Leu, and are further characterized by optional modification of the N-terminus heterocyclic nitrogen ring of $Pro^1$, preferably at the C-4 position of the heterocyclic nitrogen ring, preferably by addition of a cis- or trans-hydroxyl group or a cis- or trans-sulphydryl group, and by having the C-terminus amide group remain unmodified, which can be represented by formula (1b). Formula (1b) is depicted as:

$$R^1\text{-}Pro^1\text{-}AA^1\text{-}Gly\text{-}NH_2 \tag{1b}$$

wherein $Pro^1$, $AA^1$ and $R^1$ are as described above for formula (1). Preferred compositions of the tripeptides of formula (1b) are:

cis- or trans-4-OH-Pro-D-Arg-Gly-$NH_2$;

cis- or trans-4-OH-Pro-Ile-Gly-$NH_2$;

cis- or trans-4-OH-Pro-Arg-Gly-$NH_2$;

cis- or trans-4-OH-Pro-Trp-Gly-$NH_2$;

and, cis- or trans-4-thio-Pro-Leu-Gly-$NH_2$.

A third group of preferred compositions of the tripeptides of formula (1) which may be utilized alone or in combination with other peptides disclosed in this specification to treat patients suffering from depression are characterized by optional replacement of Leu, optional modification of the C-terminus amide group, optional modification of the C-terminus hydrogen atom at the nitrogen comprising the peptide bond between Leu-Gly, and by having the N-terminus heterocyclic nitrogen ring of $Pro^1$ remain unmodified, which can be represented by formula (1c). Formula (1c) is depicted as:

$$Pro^1\text{-}AA^1\text{-}NR^2\text{—}CH_2\text{—}R \tag{1c}$$

wherein $Pro^1$, $AA^1$, and R and $R^2$ are as described above for formula (1), with the proviso that where $Pro^1$ is Pro and $AA^1$ is Leu, $R^2$ cannot be hydrogen when R is either a carboxyl group or a hydroxyalkyl group, since the compounds of Pro-Leu-$NHCH_2$—$CO_2H$ (or Pro-Leu-Gly) and Pro-Leu-$NHCH_2$—$CH_2OH$, do not form part of this invention, and with the further proviso that where $Pro^1$ is Pro and $AA^1$ is Trp, $R^2$ cannot be a hydrogen atom when R is a hydroxyalkyl group, since Pro-Trp-$NHCH_2$—$CH_2OH$ is a known compound. Preferred compositions of the tripeptides of formula (1c) are:

Pro-Leu-$N(CH_3)CH_2$-$CONH_2$;

and,

Pro-Trp-$NHCH_2$—$CO_2H$.

In another embodiment of the invention, additional tripeptides are characterized by replacement of Leu with Arg or D-Arg; replacement of Gly with Ala; optional replacement of Pro with dehydro-Pro, preferably 3,4-dehydro-Pro; optional modification of the C-terminus amide group with a functional group selected from the group of a carboxyl group, a hydroxyalkyl group, preferably a hydroxymethyl group, an alkoxycarbonyl group, or an alkylated carbamyl group; optional modification of the N-terminus heterocyclic nitrogen ring of $Pro^1$ with a substituent selected from the group of a lower alkyl group, preferably having 1 to 3 carbon atoms, a halogen atom, preferably a fluorine or chlorine atom, a hydroxyl group, preferably a cis- or trans-4-OH—group, a sulphydryl group, preferably a cis- or trans-4-thio-group; or an alkylamino group or a dialkylamino group, preferably a methyl or ethyl amino or dimethyl or diethyl amino group; and/or optional modification of the hydrogen atoms at the nitrogen atoms of the amino acid peptide bonds with a lower alkyl group, preferably having 1 to 3 carbon atoms.

This tripeptide composition or a pharmaceutically acceptable salt thereof can be represented by the following formula (2):

$$R^1\text{-}Pro^1\text{-}AA^1\text{-}Ala\text{-}R \tag{2}$$

where $Pro^1$ represents the amino acid Pro or dehydro-Pro, preferably 3,4-dehydro Pro; $AA^1$ represents an amino acid of the group of Arg or D-Arg; R represents a carboxyl group, a hydroxyalkyl group, a carbamyl group, an alkylcarbamyl group, or an alkoxycarbonyl; and, $R^1$ represents a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

The following paragraph discloses compositions of the tripeptides of formula (2), which may be utilized alone or in combination with other peptides disclosed in this specification to treat patients suffering from depression.

A group of preferred compositions of the tripeptides of formula (2) which may be utilized alone or in combination with other peptides disclosed in this specification to treat patients suffering from depression are characterized by replacement of the Leu and Gly, and by having the N-terminus $Pro^1$ residue and C-terminus amide remain unmodified, which can be represented by formula (2a). Formula (2a) is depicted as:

$$Pro^1\text{-}AA^1\text{-}Ala\text{-}NH_2 \qquad (2a)$$

wherein $Pro^1$ and $AA^1$ are as described above for formula (2). Preferred compositions of the tripeptides of formula (2a) are:

Pro-Arg-Ala-$NH_2$;

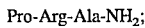

and,

Pro-D-Arg-Ala-$NH_2$.

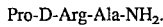

In a further embodiment according to the invention, the small tripeptides are characterized by replacement of Leu with Orn; replacement of Gly with Tyr; optional replacement of Pro with dehydro-Pro, preferably 3,4-dehydro-Pro; optional modification of the C-terminus amide group with a substituent selected from the group of a carboxyl group, a hydroxyalkyl group, preferably hydroxymethyl, an alkoxycarbonyl group, or an alkylated carbamyl group; optional modification of the N-terminus heterocyclic nitrogen ring of $Pro^1$ with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino group or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

This tripeptide composition or pharmaceutically acceptable salt thereof can be represented by the following formula (3):

$$R^1\text{-}Pro^1\text{-}AA^1\text{-}Tyr\text{-}R \qquad (3)$$

where $Pro^1$ represents the amino acid Pro or dehydro-Pro, preferably 3,4-dehydro Pro; $AA^1$ represents the amino acid Orn; R represents a carboxyl group, a hydroxyalkyl group, a carbamyl group, an alkylcarbamyl group, or an alkoxycarbonyl group; and, $R^1$ represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or dialkylamino group, preferably a methyl or ethylamino or a dimethyl or diethylamino group.

The following paragraphs disclose compositions of the tripeptides of formula (3), which may be utilized alone or in combination with other peptides disclosed in this specification to treat patients suffering from depression.

A group of preferred compositions of the tripeptides of formula (3) which may be utilized alone or in combination with other peptides disclosed in this specification to treat patients suffering from depression are characterized by replacement of Leu and Gly, optional modification of the N-terminus heterocyclic nitrogen ring of $Pro^1$, and by having the C-terminus amide remain unmodified, which can be represented by formula (3a). Formula (3a) is depicted as:

$$R^1\text{-}Pro^1\text{-}AA^1\text{-}Tyr\text{-}NH_2 \qquad (3a)$$

where $Pro^1$, $AA^1$ and $R^1$ are as described for formula (3). Preferred compositions of the tripeptides of formula (3a) are:

Pro-Orn-Tyr-$NH_2$;

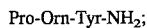

and, cis- or trans-4-OH-Pro-Orn-Tyr-$NH_2$.

In yet another embodiment according to the invention, the small peptides are tetrapeptides characterized by either addition of a C-terminus amino acid of Trp or Tyr to Gly or addition of a N-terminus amino acid of Trp or Phe to Pro to the tripeptides having the MIF core sequence; optional replacement of Leu with Ile, Arg, D-Arg, or Trp; optional replacement of Pro with dehydro-Pro, preferably 3,4-dehydro-Pro; optional modification of the C-terminus amide with a substituent selected from the group of a carboxyl group, a hydroxyalkyl group, preferably a hydroxymethyl group, an alkoxycarbonyl group, or an alkylated carbamyl group; optional modification of the heterocyclic nitrogen rings of $Pro^1$ and Trp and optional modification of the aromatic ring of Phe with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

One embodiment of the tetrapeptide compositions or pharmaceutically acceptable salt thereof including a C-terminus amino acid addition can be represented by the following formula (4):

$$R^1\text{-}Pro^1\text{-}AA^1\text{-}Gly\text{-}AA^2\text{-}R \qquad (4)$$

where $Pro^1$ represents the amino acid Pro or dehydro-Pro, preferably 3,4-dehydro Pro; $AA^1$ represents an amino acid of the group of Ile, Leu, Arg, D-Arg or Trp; $AA^2$ represents Trp or Tyr; R represents a carboxyl group, hydroxyalkyl group, a carbamyl group, an alkylcarbamyl group, or an alkoxycarbonyl group; and, $R^1$ represents a hydrogen atom, a lower alkyl group, preferably having 1 to 3 carbon atoms, a dehydro group, a halogen atom, preferably a fluorine or chlorine atom, a hydroxyl group, a sulphydryl group, or an alkylamino or dialkylamino group, preferably a methyl or ethylamino or dimethyl or diethylamino group.

The following paragraphs disclose compositions of the tetrapeptides of formula (4), which may be utilized alone or in combination with other peptides disclosed in this specification to treat patients suffering from depression.

A group of preferred compositions of the tetrapeptides of formula (4) which may be utilized alone or in combination with other peptides disclosed in this specification to treat patients suffering from depression are characterized by addition of Trp or Tyr to the C-terminus Gly, by optional replacement of Leu, by optional modification of the N-terminus heterocyclic nitrogen ring of Pro¹, and by having the C-terminus amide remain unmodified, which can be represented by formula (4a). Formula (4a) is depicted as:

R¹-Pro-AA¹-Gly-AA²-NH₂ (4a)

wherein Pro¹, AA¹, AA², and R¹ are as described for formula (4). Preferred compositions of the tetrapeptides of formula (4a) are:

cis- or trans-4-OH-Pro-Leu-Gly-Trp-NH₂ (SEQ ID NO: 1)

cis- or trans-4-OH-Pro-Ile-Gly-Trp-NH₂ (SEQ ID NO: 2)

cis- or trans-4-OH-Pro-D-Arg-Gly-Trp-NH₂;

and, 3,4-dehydro-Pro-D-Arg-Gly-Trp-NH₂.

A second group of preferred compositions of the tetrapeptides of formula (4) which may be utilized alone or in combination with other peptides disclosed in this specification to treat patients suffering from depression are characterized by addition of Trp or Tyr to the C-terminus Gly, by optional replacement of Leu, and by having the N-terminus heterocyclic nitrogen ring of Pro¹ remain unmodified, which can be represented by formula (4b). Formula (4b) is depicted as:

Pro¹-AA¹-Gly-AA²-NH₂ (4b)

wherein Pro¹, AA¹ and AA² are as described for formula (4). Preferred compositions of the tetrapeptides of formula (4b) are:

Pro-Ile-Gly-Trp-NH₂ (SEQ ID NO: 3);

3,4-dehydro-Pro-Ile-Gly-Trp-NH₂ (SEQ ID NO: 4);

Pro-Leu-Gly-Trp-NH₂ (SEQ ID NO: 5);

Pro-Leu-Gly-Tyr-NH₂ (SEQ ID NO: 6);

Pro-Arg-Gly-Trp-NH₂ (SEQ ID NO: 7);

Pro-Trp-Gly-Trp-NH₂ (SEQ ID NO: 8);

Pro-D-Arg-Gly-Trp-NH₂;

and,

Pro-Ile-Gly-Tyr-NH₂ (SEQ ID NO: 9).

Another embodiment of the tetrapeptide compositions or pharmaceutically acceptable salt thereof including a N-terminus amino acid addition can be represented by the following formula (5):

R¹-AA¹-R²-Pro¹-AA²-Gly-R (5)

where Pro¹ represents the amino acid Pro or dehydro-Pro, preferably 3,4-dehydro Pro; AA¹ represents an amino acid of the group of Trp, Tyr, or Phe; AA² represents an amino acid of the group of Leu, Ile, or Trp; R represents a carboxyl group, hydroxyalkyl group, a carbamyl group, an alkylcarbamyl group, or an alkoxycarbonyl group; and, R¹ and R² each independently represent a hydrogen atom, a lower alkyl group, preferably having 1 to 3 carbon atoms, a halogen atom, preferably a fluorine or chlorine atom, a hydroxyl group, a sulphydryl group, or an alkylamino or dialkylamino group, preferably a methyl or ethylamino or dimethyl or diethylamino group.

The following paragraphs disclose compositions of the tetrapeptides of formula (5), which may be utilized alone or in combination with other peptides disclosed in this specification to treat patients suffering from depression.

A group of preferred compositions of the tetrapeptides of formula (5) which may be utilized alone or in combination with other peptides disclosed in this specification to treat patients suffering from depression are characterized by addition of Trp, Tyr, or Phe to the N-terminus Pro¹, optional replacement of Leu, optional modification of the heterocyclic nitrogen rings of Pro¹ and Trp and optional modification of the aromatic ring of Phe and Tyr, and by having the C-terminus amide remain unmodified, which can be represented by formula (5a). Formula (5a) is depicted as:

R¹-AA¹-R²-Pro¹-AA²-Gly-NH₂ (5a)

wherein Pro¹, AA¹, AA², R¹, and R² are as described for formula (5), with the proviso that where Pro¹ is Pro, R¹ and R² cannot both be a hydrogen atom when AA¹ is Tyr and AA² is Trp, since Tyr-Pro-Trp-Gly-NH₂ is a known compound, and with the further proviso that where Pro¹ is Pro and AA² is Leu, R¹ and R² cannot both be a hydrogen atom when AA¹ is Phe or Tyr, since Phe-MIF-1 and Tyr-MIF-1 are known compounds. Preferred compositions of the tetrapeptides of formula (5a) are:

Trp-Pro-Leu-Gly-NH₂ (SEQ ID NO: 10);

Phe-Pro-Leu-Gly-NH₂ (SEQ ID NO: 11)

4-F-Phe-Pro-Leu-Gly-NH₂ (SEQ ID NO: 12);

4-Cl-Phe-Pro-Leu-Gly-NH₂ (SEQ ID NO: 13);

4-F-Phe-Pro-Ile-Gly-NH₂ (SEQ ID NO: 14);

4-F-Phe-cis- or trans-4-OH-Pro-Leu-Gly-NH₂ (SEQ ID NO: 15);

4-F-Phe-cis- or trans-4-OH-Pro-Ile-Gly-NH₂ (SEQ ID NO: 16);

Trp-Pro-Leu-Gly-NH₂ (SEQ ID NO: 17);

Trp-Pro-Ile-Gly-NH₂ (SEQ ID NO: 18);

Trp-cis- or trans-4-OH-Pro-Leu-Gly-NH₂ (SEQ ID NO: 19);

and,

Trp-cis- or trans-4-OH-Pro-Ile-Gly-NH₂ (SEQ ID NO: 20);

In yet another embodiment of the invention, the peptides are pentapeptides with either addition of two N-terminus amino acids of Phe, Tyr, Leu, or Ile to Pro¹, addition of a N-terminus amino acid of Phe or Tyr to Pro¹ and a C-terminus amino acid addition of Trp to Gly, or addition of a C-terminus amino acids of Trp to Gly and an internal amino acid between Pro¹ and Gly, to tripeptides having the MIF core sequence; optional replacement of Leu with Ile or Trp; optional replacement of Pro with dehydro-Pro, preferably 3,4-dehydro-Pro; optional modification of the C-terminus amide with a substituent selected from the group of a carboxyl group, a hydroxyalkyl group, preferably a hydroxymethyl group, an alkoxycarbonyl group, or an alkylated carbamyl group; optional modification of the heterocyclic nitrogen ring of Pro¹ and optional modification of the aromatic rings of Tyr or Phe with a substituent selected from the group of a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or a dialkylamino group, preferably a methyl or ethylamino or a dimethyl or diethylamino group; and/or optional modification of the hydrogen atoms at the nitrogen atoms of the amino acid peptide bonds with a lower alkyl group, preferably having 1 to 3 carbon atoms.

One embodiment of the pentapeptide compositions including addition of two N-terminus amino acids or pharmaceutically acceptable salt thereof can be represented by the following formula (6):

$$R^1-AA^1-AA^2-R^2-Pro^1-AA^3-Gly-R \qquad (6)$$

where Pro¹ represents the amino acid Pro or dehydro-Pro, preferably 3,4-dehydro Pro; AA¹ and AA² each independently represent an amino acid of the group of Phe or Tyr; AA³ represents an amino acid of the group of Leu or Ile; R represents a carboxyl group, hydroxyalkyl group, a carbamyl group, all alkylcarbamyl group, or an alkoxycarbonyl group; and, R¹ and R² each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or dialkylamino group, preferably a methyl or ethylamino or dimethyl or diethylamino group. The following paragraph discloses compositions of the pentapeptides of formula (6), which may be utilized alone or in combination with other peptides disclosed in this specification to treat patients suffering from depression.

A group of preferred compositions of the pentapeptides of formula (6) which may be utilized alone or in combination with other peptides disclosed in this specification to treat patients suffering from depression are characterized by addition of two N-terminus amino acids of Phe and Tyr to Pro¹, optional modification of the heterocyclic nitrogen ring of Pro¹ and optional modification of the aromatic rings of Phe or Tyr, optional replacement of Leu, and by having the C-terminus amide of Gly remain unmodified, which can be represented by formula (6a). Formula (6a) is depicted as:

$$R^1-AA^1-AA^2-R^2-Pro^1-AA^3-Gly-NH_2 \qquad (6a)$$

wherein Pro¹, ᴬᴬ¹, AA², R¹, and R² are as described for formula (6). Preferred pentapeptides of formula (6a) are:

4-F-Phe-Tyr-Pro-Leu-Gly-NH₂ (SEQ ID NO: 21);

4-Cl-Phe-Tyr-Pro-Leu-Gly-NH₂ (SEQ ID NO: 22);

Phe-Tyr-Pro-Leu-Gly-NH₂ (SEQ ID NO: 23);

Phe-Tyr-Pro-Ile-Gly-NH₂ (SEQ ID NO: 24);

Phe-Tyr-cis- or trans-4-OH-Pro-Leu-Gly-NH₂ (SEQ ID NO: 25);

Phe-Tyr-cis- or trans-4-OH-Pro-Ile-Gly-NH₂ (SEQ ID NO: 26);

Tyr-Tyr-Pro-Leu-Gly-NH₂ (SEQ ID NO: 27);

Tyr-Tyr-Pro-Ile-Gly-NH₂ (SEQ ID NO: 28);

Tyr-Tyr-cis- or trans-4-OH-Pro-Leu-Gly-NH₂ (SEQ ID NO: 29);

and,

Tyr-Tyr-cis- of trans-4-OH-Pro-Ile-Gly-NH₂ (SEQ ID NO: 30).

In another embodiment of the invention, pentapeptide compositions or pharmaceutically acceptable salt thereof including addition of both a N-terminus amino acid and a C-terminus amino acid can be represented by the following formula (7):

$$R^1-AA^1-R^2-Pro^1-AA^2-Gly-AA^3-R \qquad (7)$$

where Pro¹ represents the amino acid Pro or dehydro-Pro, preferably 3,4-dehydro Pro; AA¹ represents an amino acid of the group of Phe or Tyr; AA³ represents an amino acid of the group of Leu, Ile, Arg, D-Arg, or Trp; AA³ represents the amino acid Trp; R represents a carboxyl group, hydroxyalkyl group, a carbamyl group, an alkylcarbamyl group, or an alkoxycarbonyl group; and, R¹ and R² each independently represent a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or dialkylamino group, preferably a methyl or ethylamino or dimethyl or diethylamino group.

The following paragraph discloses compositions of the pentapeptides of formula (7), which may be utilized alone or in combination with other peptides disclosed in this specification to treat patients suffering from depression.

A group of preferred compositions of the pentapeptides of formula (7) which may be utilized alone or in combination with other peptides disclosed in this specification to treat patients suffering from depression are characterized by addition of a N-terminus amino acid of Phe or Tyr to Pro¹, addition of a C-terminus amino acid of Trp to Gly, optional modification of the heterocyclic nitrogen ring of Pro¹ and optional modification of the aromatic rings of Phe or Tyr, optional replacement of Leu with Ile, Arg, D-Arg, or Trp, and by having the C-terminus amide remain unmodified, which can be represented by formula (7a). Formula (7a) is depicted as:

$$R^1-AA^1-R^2-Pro^1-AA^2-Gly-Trp-NH_2 \qquad (7a)$$

wherein Pro¹, AA¹, AA², R¹, and R² are as described for formula (7). Preferred pentapeptides of formula (7a) are:

Phe-Pro-Leu-Gly-Trp-NH₂ (SEQ ID NO: 31);

Tyr-Pro-Leu-Gly-Trp-NH₂ (SEQ ID NO: 32);

Phe-cis- or trans-4-OH-Pro-Leu-Gly-Trp-NH₂ (SEQ ID NO: 33);

Phe-Pro-Ile-Gly-Trp-NH₂ (SEQ ID NO: 34);

Phe-cis- or trans-4-OH-Pro-Ile-Gly-Trp-NH₂ (SEQ ID NO: 35);

Tyr-cis- or trans-4-OH-Pro-Leu-Gly-Trp-NH₂ (SEQ ID NO: 36);

Tyr-Pro-Ile-Gly-Trp-NH₂ (SEQ ID NO: 37);

Tyr-cis- or trans-4-OH-Pro-Leu-Gly-Trp-NH₂ (SEQ ID NO: 38);

Tyr-Pro-Trp-Gly-Trp-NH₂ (SEQ ID NO: 39);

Tyr-cis- or trans-4-OH-Pro-Trp-Gly-Trp-NH₂ (SEQ ID NO: 40);

4-F-Phe-cis or trans-4-OH-Pro-Ile-Gly-Trp-NH₂ (SEQ ID NO: 41);

4-F-Phe-cis- or trans-4-OH-Pro-Leu-Gly-Trp-NH₂ (SEQ ID NO: 42);

4-F-Phe-cis- or trans-4-OH-Pro-Arg-Gly-Trp-NH2 (SEQ ID NO: 43);

and,

4-F-Phe-cis- or trans-4-OH-Pro-D-Arg-Gly-Trp-NH$_2$.

In yet another embodiment of the invention, pentapeptide compositions or pharmaceutically acceptable salt thereof including addition of a C-terminus amino acid and an internal amino acid can be represented by the following formula (8):

R$^1$-Pro$^1$-AA$^1$-AA$^2$-Gly-AA$^3$-R     (8)

where Pro$^1$ represents the amino acid Pro or dehydro-Pro, preferably 3,4-dehydro Pro; AA$^1$ and AA$^2$ each independently represent an amino acid of the group of Leu or Ile; AA$^3$ represents Trp; R represents a carboxyl group, a hydroxyalkyl group, a carbamyl group, an alkylcarbamyl group, or an alkoxycarbonyl group; and, R$^1$ represents a hydrogen atom, a lower alkyl group, preferably having 1 to 3 carbon atoms, a halogen atom, preferably a fluorine or chlorine atom, a hydroxyl group, preferably a cis- or trans-4-OH— group, a sulphydryl group, preferably a cis- or trans-4-thio-group, or an alkylamino or dialkylamino group, preferably a methyl or ethylamino group or dimethyl or diethylamino group.

The following paragraph discloses compositions of the pentapeptides of formula (8), which may be utilized alone or in combination with other peptides disclosed in this specification to treat patients suffering from depression.

A group of preferred compositions of the pentapeptides of formula (8) which may be utilized alone or in combination with other peptides disclosed in this specification to treat patients suffering from depression are characterized by addition of a C-terminus amino acid of Trp to Gly, addition of an internal amino acid of Leu or Ile between Pro$^1$ and Gly, optional modification of the heterocyclic nitrogen ring of Pro$^1$, optional replacement of Leu with Ile, and by having the C-terminus amide remain unmodified, which can be represented by formula (8a). Formula (8a) is depicted as:

R$^1$-Pro$^1$-AA$^1$-AA$^2$-Gly-Trp-NH$_2$     (8a)

wherein Pro$^1$, AA$^1$, AA$^2$, and R$^1$ are as described for formula (8). Preferred pentapeptides of formula (8a) are:

Pro-Ile-Leu-Gly-Trp-NH$_2$ (SEQ ID NO: 44), and, cis- or trans-4-OH -Pro-Ile-Leu-Gly-Trp-NH$_2$ (SEQ ID NO: 45).

In yet another embodiment of the invention, the peptides are polypeptides including chemical combinations and/or overlapping chemical combinations of any of the small peptides of any of formula (1) through formula (8) described above which may be utilized alone or in combination with other peptides disclosed in this specification to treat patients suffering from depression. The chemical combinations and/or overlapping chemical combinations of the peptides disclosed preferably range from at least about three to at least about ten amino acids. Examples of such combinations include, but are not necessarily limited to, the compositions as follows: 4-F-Phe-cis- or trans-4-OH-Pro-Ile-Gly-Trp-Gly-NH$_2$(SEQ ID NO: 46), 4-F-Phe-cis or trans-4-OH-Pro-Ile-Gly-Trp-Gly-Trp-NH$_2$ (SEQ ID NO: 47), 4-F-Phe-cis- or trans-4-OH-Pro-Leu-Gly-Trp-Gly-NH$_2$ (SEQ ID NO: 48), 4-F-Phe-cis- or trans-4-OH-Pro-Leu-Gly-Trp-Gly-Trp-NH$_2$ (SEQ ID NO: 49), Pro-Ile-Gly-Trp-Pro-Ile-Gly-NH$_2$ (SEQ ID NO: 50), 4-F-Phe-cis- or trans-4-OH-Pro-Arg-Gly-Trp-Gly-NH$_2$ (SEQ ID NO: 51), 4-F-Phe-cis- or trans-4-OH-Pro-Arg-Gly-Trp-Gly-Trp-NH$_2$ (SEQ ID NO: 52), 4-OH-Pro-Ile-Gly-4-OH-Pro-Ile-Gly-NH$_2$ (SEQ ID NO: 53), 3,4-dehydro-Pro-D-Arg-Gly-3,4-dehydro-Pro-D-Arg-Gly-NH$_2$; 3,4-dehydro-Pro-D-Arg-Gly-Trp-Gly-NH$_2$; and, 3,4-dehydro-Pro-D-Arg-Gly-Trp-Gly-Trp-NH$_2$.

The small peptides with which this invention is concerned are readily prepared by conventional procedures (i.e., carbodiimide method, mixed anhydride method, N,N-carbonyldiimidazole method) for the step-wise synthesis of polypeptides, and also including solid phase peptide synthesis. The substituents groups are also readily added to the polypeptide residues by conventional procedures.

The small peptides of the invention possess antidepressant activity as determined by the Porsolt swim test as described in the Example Section. The Porsolt swim test is based on the observation that when a rat is forced to swim in a situation from which there is no escape, the rat ceases to move altogether and makes only those movements necessary to keep its head above water. Immobility indicates a state of despair. Therefore, a compound with activity as an antidepressant will delay the onset of immobility.

The active ingredient, which may comprise one or more of the peptides disclosed in the present invention, should be formulated in a suitable pharmaceutical carrier for vivo administration to the patient by any standard method known in the art. Appropriate routes of administration include, but are not limited to, oral (mouth or peroral administration), sublingual, parenteral (e.g., intravenous, intraspinal, intrathecal, intraventricular, epidermal, intracisternal, intracutaneous or intradermal, subcutaneous, or intramuscular), epicutaneous or transdermal, intranasal or rectal as well as inhalation (poly or mircodispersed aerosol).

As with other pharmaceutical delivery strategies, the primary dosage form depends on the mode of administration. Oral administration includes, but is not limited to tablets, capsules, solutions, suspensions, gels, powders, elixirs or syrups. Sublingual administration includes but is not limited to tablets or lozenges. Parenteral administration includes but is not limited to solutions and suspensions. Epicutaneous or transdermal application will include, but are not necessarily limited to, ointments, creams, pastes, plasters, powders, aerosols, lotions, transdermal patches, discs and solutions. Intranasal administration of the peptide or peptides of the present invention include, but are not limited to, solutions, sprays, inhalants or ointments. Rectal administration may include, but is not necessarily limited to, solutions, ointments or suppositories. The active ingredient may also be formulated for incorporation into liposomes, microcapsules, polymer or wax-based and controlled release preparations. For additional guidance regarding routes of administration and the generation of pharmaceutically effective dose rates, see Chapter 3—"Dosage Form Design: Biopharmaceutical Considerations" in Pharmaceutical Dosage Forms and Drug Delivery Systems, 1990, Ansel, H. C. and Popovich, N. G., Fifth Ed.; Lea and Febiger, Philadelphia.

The concentration of the peptide(s) used in any of the aforementioned formulations will depend upon the effective dose and the mode of administration used to elicit the appropriate biological effect. The dose should be sufficient to achieve circulating plasma concentrations of the active ingredient such that effective amounts cross the blood-brain barrier that are efficacious. For example, when the tetrapeptide Pro-Leu-Gly-Trp-NH$_2$ is the active ingredient, a circulating plasma level from about 30 mg to about 90 mg per average adult may be used; preferably about 60 mg per average adult. Effective doses for various routes of administration may be extrapolated from dose-response curves derived from in vitro or animal model test systems.

The invention will be further clarified by a consideration of the following examples, which are intended to be purely exemplary of the synthesis and use of the small peptides of the invention.

6. EXAMPLE

A TRI-TETRA- OR PENTA-PEPTIDE AS AN ANTIDEPRESSANT

6.1. MATERIALS AND METHODS

6.1.1. PEPTIDE SYNTHESIS

Small peptides of the present invention were synthesized by methods known to one of ordinary skill in the art. Briefly, 5 mm of Rink amide resin is placed in a reaction vessel of an Applied Biosystem 431A peptide synthesizer. Double couple cycles were used since the amount of starting resin was twice that of a standard run. The following steps were then carried out: (1) the Fmoc blocking group on the resin was first removed by washing with 20% piperidine; (2) the resin is then washed with N-methylpyrrolidinone; (3) 2 mM Fmoc-proline was added to the reaction vessel together with 0.45 mm 2-(1H-benzotriazol-1-yl)-1,1,3,3,-tetramethyluronium hexafluorophosphate in a solution of 1-hydroxybenzotriazole and 1 mM of diisopropylethylamine; (4) the resin was washed with N-methylpyrrolidinone; (5) the cycle was repeated with Fmoc-leucine, then with Fmoc-glycine and finally with Fmoc-tryptophan; (6) the peptide resin bond was cleaved with the following solution: 0.25 ml ethanedithiol, 0.25 ml $H_2O$, and 9.5 ml TFA, with a cleavage time of 3–4 hours; (7) the peptide was then purified by two reverse phase HPLC procedures, the first in 0.1% TFA in water as the eluting solvent and the second using 0.1% TFA in acetonitrile as the eluting solvent.

The purity of synthesized peptides was analyzed using a HP1090L analytical HPLC equipped with a diode ray. A UV trace showing absorption of the peptide from 220 nm to 310 nm was plotted. Molecular weights were verified by mass spectrometry.

The purity of synthesized peptides was analyzed using a HP1090L analytical HPLC equipped with a diode ray. A UV trace showing absorption of the peptide from 220 nm to 3 10 nm was plotted. Molecular weights were verified by mass spectrometry.

6.1.2. SYNTHESIS OF PRO-ARG-GLY-$NH_2$

Pro-Arg-Gly-$NH_2$ was synthesized manually using a fritted funnel with the step sequence given as for synthesis of Pro-Leu-Gly-Trp-$NH_2$ (SEQ ID NO:5) and the appropriate Fmoc-amino acids. Regarding synthesis of Pro-Arg-Gly-$NH_2$, dimethylformamide was used in place of N-methylpyrrolidinone, and in step (6) the peptide resin bond was cleaved using the following solvent mixture: 0.75 g phenol in 0.25 ml thioanisole, 0.5 ml $H_2O$ and 10 ml TFA.

The other peptides disclosed in this specification, except the tripeptide Pro-Arg-Gly-$NH_2$, were prepared as described in Section 6.1.2.

One of ordinary skill in the art could utilize any of a number of known techniques for synthesizing the peptides of the present invention.

Each purified peptide was stored frozen as a white crystalline powder. MIF was also synthesized by techniques known to one of ordinary skill in the art. This tripeptide was stored frozen as a white crystalline powder.

6.1.3. VARIATION OF THE PORSOLT SWIM TEST TO IDENTIFY PEPTIDES WITH ANTIDEPRESSANT ACTIVITY

Male Sprague Dawley rats were obtained from Charles River Laboratories, Wilmington, Mass. The rats were housed individually in stainless steel one half inch wire mesh cages sized in accordance with the "Guide for the Care and Use of Laboratory Animals" of the Institute of Laboratory Animals Resources National Research and Counsel. The animal rooms were kept under a twelve hour light/ twelve hour dark cycle, with temperature maintained at 18° to 26° C. and relative humidity at 40% to 70%. The test animals were acclimated for a minimum of seven days prior to initiation of the study. Daily doses of the small peptides of the present invention were prepared by dissolving 1 mg q.s. to 10.0 ml 0.01M acetic acid in 0.9% saline. 1 ml/kg of the respective peptide was then administered by intraperitoneal injection once a day for five consecutive days.

The antidepressant activity of the peptides of the present invention was determined by a variation of the Porsolt swim test (Porsolt, et al., 1977, Nature 266: 730–732). The method is based on the observation that a rat, when forced to swim in a situation from which there is no escape, will, after an initial period of vigorous activity, eventually cease to move altogether and make only those movements necessary to keep its head above water. Immobility indicates a state of despair in which the conditioned rat cannot escape and resigns itself to the experimental situation. On the first day of the study, the animals were plunged individually into a vertical plexiglass cylinder (40 cm in height and 18 cm in diameter) containing 24 cm of water maintained at 25°–26° C. The cylinder was painted white. The water was changed between each rat. After 15 minutes in the cylinder the rats were removed and returned to their individual cages without being dried. One hour later the rats were administered the tetrapeptide, MIF or a control (0.01M acetic acid in 0.9% saline), based on individual body weight. On days 2, 3, and 4, at the time of day that corresponds to the average injection time of the entire study group of animals, the rats were injected with either peptide 1–39 or the control solution. On day 5, after being weighed each individual rat was respectively dosed based on individual body weight. Doses were staggered in such a manner as to provide ample time for test evaluation to be conducted between animals. Fifteen minutes following injection, each rat was placed in the water for 300 seconds. The mobile time for each rat was recorded.

6.2. RESULTS

Table 1 (compounds 1–43) and FIGS. 1–3 (compounds 1–24) depict results generated from numerous Porsolt swim tests administered with peptides of the present invention, known antidepressant compounds (e.g., compound #6 [amitriptyline], compound #20, fluoxetine [Prozac], compound #24, and sertraline [Zoloft]), known compounds (e.g., compound #14 and compound #32), and a placebo (CGI: 0.1M acetic acid in 0.9% saline at 1 ml/kg).

Table 1 and FIGS. 1–3 disclose peptides in a consistent numerical fashion which correspond to the respective SEQ ID NO's as follows:

| Peptide # | SEQ ID NO: |
| --- | --- |
| 1 | 43 |
| 2 | 41 |
| 3 | 16 |
| 4 | 3 |
| 5 | 42 |
| 8 | 15 |
| 13 | 12 |
| 16 | 39 |
| 23 | 5 |
| 25 | 1 |
| 26 | 11 |
| 29 | 7 |
| 31 | 2 |
| 34 | 8 |
| 35 | 17 |
| 36 | 6 |
| 37 | 32 |
| 39 | 27 |
| 40 | 23. |

The number of responding animals out of a possible 12 animals utilized in each test group is reported in column 3 of Table 1 and in FIG. 1. FIG. 1 provides a graphical analysis of the average number of responding animals out of a possible 12 animals compiled in one or more experimental groups. A responding animal is defined as an animal whose mobile time during the 300 second exposure to the water tank was of longer duration than the average mobile time of the CGI group plus one standard deviation. For example, if the average mobile time for CGI group of twelve treated rats is 35 seconds plus or minus one standard deviation of 15 seconds, then a responding animal is defined as an animal exhibiting a mobile time greater than fifty seconds. Therefore, the control group mean plus one standard deviation was taken as a threshold for response; the number of rats with mobile times exceeding this level is tabulated as a responding animal.

Table 1 (column 4) gives the difference between the mobile times of the compounds 1–43 and the mobile time of CGI. The average of mean mobile time for each peptide are presented. The average mean mobile time between experimental groups for each peptide, represented by a double asterisk, is also presented as part of FIG. 2. FIG. 2 illustrates the mean of mobile time for peptides #1–5, #7–19, #21–23, antidepressant compounds #6, #14, #24 as well as compound #14. The treatment means were compared with control (CGI) means by a one-tailed Student's t-test. The probabilities so obtained are given in Table 1 (column 5).

The Z-score of for mean of mobile time for compounds 1–43, reported in FIG. 3 and/or Table 1 (at column 6) is a dimensionless measure of efficacy that was averaged over the numerous studies. The mean of Z-score is defined as the difference between the treatment group's mean mobile time and the control group's mean mobile time, divided by the standard deviation of the mean mobile time of the control group. Therefore, an inefficacious compound were generate a Z-score near zero, and higher Z-scores denote increasing efficacy.

Table 1 and the graphic representation of data for peptides #1–5, #7–19, #21–23, antidepressant compounds #6, #14, #24 as well as compound #14 in FIGS. 1–3 indicate that numerous peptides of the present invention exhibit antidepressant activity in comparison to known antidepressant compounds such as amitriptyline, Prozac and Zoloft. Additionally, the vast majority of the exemplified peptides of the present invention show greater activity than MIF. Therefore, Applicants disclose a number of small peptides for use as antidepressant compounds, with biological data to support such use.

Other embodiments of the invention will be apparent to those persons skilled in the art from a consideration of this specification or practice of the invention disclosed herein. It is intended that the specification and examples be considered as exemplary only, with the true scope and spirit of the invention to which exclusive rights are claimed being assessed by the appended claims.

TABLE 1

| No. 1 | Structure 2 | No. of Responders 3 | Difference Between Means of Mobile Time for Drug & CGI 4 | Probability of t-Test Difference for Mobile Time Between Drug & CGI 5 | Z-Score for Mean of Mobile Time for Drug vs. CGI 6 |
| --- | --- | --- | --- | --- | --- |
| 1 | 4-F—Phe-4-OH—Pro—Arg—Gly—Trp—NH$_2$ (SEQ ID NO: 43) | 12 | 43.50 | 0.0001* | 4.88 |
| | | 12 | 56.75 | 0.0001* | 6.51 |
| | | | 50.13** | | 5.70*** |
| 2 | 4-F—Phe-4-OH—Pro—Ile—Gly—Trp—NH$_2$ (SEQ ID NO: 41) | 11 | 33.25 | 0.0001* | 3.73 |
| | | 11 | 35.83 | 0.0001* | 4.11 |
| | | | 34.54** | | 3.92*** |
| 3 | 4-F-Phe-4-OH—Pro—Ile—Gly—NH$_2$ (SEQ ID NO: 16) | 9 | 24.00 | 0.0014* | 1.67 |
| | | 12 | 31.58 | 0.0002* | 4.40 |
| | | 12 | 23.08 | 0.0000* | 3.44 |
| | | 8 | 20.08 | 0.0029* | 1.62 |
| | | | 24.68** | | 2.78*** |
| 4 | Pro—Ile—Gly—Trp—NH$_2$ (SEQ ID NO: 3) | 12 | 41.75 | 0.0000* | 3.71 |
| | | 11 | 24.59 | 0.0001* | 2.06 |
| | | 7 | 29.50 | 0.0046* | 2.19 |
| | | 11 | 27.17 | 0.0001* | 2.20 |
| | | | 30.79** | | 2.54*** |
| 5 | 4-F-Phe-4-OH—Pro—Leu—Gly—Trp—NH$_2$ (SEQ ID NO: 42) | 10 | 2.70 | 0.0016* | 3.03 |
| | | | 2.70** | | 3.03*** |
| 6 | Amitriptyline | 11 | 76.83 | 0.0001* | 2.78 |
| | | 12 | 54.50 | 0.0005* | 4.10 |
| | | 8 | 33.58 | 0.0016* | 1.88 |
| | | 10 | 40.08 | 0.0003* | 2.24 |
| | | 9 | 70.58 | 0.0002* | 7.36 |
| | | 11 | 60.92 | 0.0000* | 3.09 |
| | | 9 | 56.92 | 0.0081* | 3.01 |
| | | 3 | 12.92 | 0.3581 | 0.43 |

TABLE 1-continued

| No. 1 | Structure 2 | No. of Responders 3 | Difference Between Means of Mobile Time for Drug & CGI 4 | Probability of t-Test Difference for Mobile Time Between Drug & CGI 5 | Z-Score for Mean of Mobile Time for Drug vs. CGI 6 |
|---|---|---|---|---|---|
| | | 8 | 56.00<br>51.37** | 0.0081* | 1.87<br>2.97*** |
| 7 | 4-F-Phe-4-OH—Pro—D—Arg—Gly—Trp—NH$_2$ | 9 | 17.58<br>17.58** | 0.0020* | 2.02<br>2.02*** |
| 8 | 4-F-Phe-4-OH—Pro—Leu—Gly—NH$_2$<br>(SEQ ID NO: 15) | 10<br>8<br>8 | 29.83<br>24.00<br>27.67<br>27.17** | 0.0002*<br>0.0006*<br>0.0009* | 2.12<br>1.73<br>1.60<br>1.82*** |
| 9 | 3,4-Dehydro-Pro—D—Arg—Gly—NH$_2$ | 9<br>11<br>6 | 30.00<br>46.08<br>8.17<br>28.08 | 0.0052*<br>0.0037*<br>0.1179 | 2.16<br>6.42<br>1.22<br>3.27*** |
| 10 | 4-OH—Pro—D—Arg—Gly—Trp—NH$_2$ | 8<br>9<br>7 | 18.41<br>22.17<br>15.50<br>18.69** | 0.0011*<br>0.0041*<br>0.0156* | 1.63<br>3.09<br>1.26<br>1.99*** |
| 11 | 4-OH—Pro—Ile—Gly—NH$_2$ | 8<br>8 | 30.25<br>14.08<br>22.17** | 0.0078*<br>0.0107* | 2.11<br>2.10<br>2.10*** |
| 12 | 4-OH—Pro—D—Arg—Gly—NH$_2$ | 6<br>11<br>10<br>3 | 18.25<br>43.75<br>36.16<br>6.67<br>26.21** | 0.0181*<br>0.0001*<br>0.0001*<br>0.2953 | 1.30<br>3.52<br>3.21<br>0.39<br>2.10*** |
| 13 | 4-F—Phe—Pro—Leu—Gly—NH$_2$<br>(SEQ ID NO: 12) | 10<br>6<br>6 | 33.00<br>17.16<br>14.00<br>21.39** | 0.0011*<br>0.0170*<br>0.0172* | 2.94<br>1.22<br>1.12<br>1.76*** |
| 14 | Pro—D—Leu—Gly—NH$_2$ | 7 | 15.00<br>15.00** | 0.0667 | 1.07<br>1.07*** |
| 15 | Pro—Leu—Sar—NH$_2$ | 6 | 15.41<br>15.41** | 0.0585 | 0.95<br>0.95*** |
| 16 | Tyr—Pro—Trp—Gly—Trp—NH$_2$<br>(SEQ ID NO: 39) | 6 | 9.92<br>9.92** | 0.0582 | 0.88<br>0.88*** |
| 17 | 4-OH—Pro—Arg—Gly—NH$_2$ | 4<br>7 | 28.58<br>25.83<br>27.21** | 0.0308*<br>0.0038* | 1.28<br>1.59<br>1.43*** |
| 18 | Pro—D—Arg—Gly—NH$_2$ | 6<br>7<br>7<br>2 | 24.92<br>21.92<br>28.50<br>3.83<br>19.79** | 0.0337*<br>0.0057*<br>0.0034*<br>0.5546 | 1.30<br>1.67<br>1.15<br>0.24<br>1.09*** |
| 19 | 4-OH—Pro—Trp—Gly—NH$_2$ | 10<br>1 | 41.98<br>−4.34<br>18.82** | 0.0097*<br>0.4195 | 3.74<br>−0.31<br>1.71*** |
| 20 | Zoloft | 5<br>5<br>6<br>6<br>5 | 27.67<br>17.17<br>16.42<br>24.92<br>20.42<br>21.32** | 0.0896<br>0.0521<br>0.0080*<br>0.0269*<br>0.2057 | 1.44<br>1.31<br>1.13<br>1.18<br>1.01<br>1.21*** |
| 21 | Pro—Arg—Gly—NH$_2$ | 5<br>6<br>5 | 16.83<br>31.17<br>24.00<br>24.00** | 0.0886<br>0.0280*<br>0.0252* | 0.97<br>1.97<br>1.14<br>1.36*** |
| 22 | Pro—Orn—Gly—NH$_2$ | 5 | 24.75<br>24.75** | 0.0696 | 1.71<br>1.71*** |
| 23 | Pro—Leu—Gly—Trp—NH$_2$<br>(SEQ ID NO: 5) | 6<br>2<br>5<br>5<br>7<br>5 | 39.09<br>10.25<br>20.08<br>16.25<br>18.92<br>15.67<br>20.04** | 0.0727*<br>0.2553<br>0.1268<br>0.0355*<br>0.0243*<br>0.0837 | 2.18<br>0.41<br>0.67<br>0.86<br>1.19<br>0.74<br>1.01*** |
| 24 | Prozac | 6<br>3<br>4<br>6<br>5 | 21.42<br>19.08<br>11.75<br>18.09<br>24.25<br>18.92** | 0.0282*<br>0.0397*<br>0.1020<br>0.0200*<br>0.0389* | 1.11<br>1.01<br>0.68<br>1.14<br>1.50<br>1.09*** |
| 25 | 4-O—Pro—Leu—Gly—Trp—NH$_2$<br>(SEQ ID NO: 1) | 6<br>3 | 33.83<br>4.25 | 0.0059*<br>0.3288 | 1.37<br>0.34 |

TABLE 1-continued

| No. 1 | Structure 2 | No. of Responders 3 | Difference Between Means of Mobile Time for Drug & CGI 4 | Probability of t-Test Difference for Mobile Time Between Drug & CGI 5 | Z-Score for Mean of Mobile Time for Drug vs. CGI 6 |
|---|---|---|---|---|---|
|  |  |  | 19.04** |  | 0.86*** |
| 26 | Phe—Pro—Leu—Gly—NH$_2$ (SEQ ID NO: 11) | 6 | 11.33 | 0.0931 | 0.77 |
|  |  | 3 | 20.67 | 0.3057 | 0.76 |
|  |  |  | 16.00** |  | 0.76*** |
| 27 | Pro—Arg—Ala—NH$_2$ | 4 | 18.58 | 0.0268* | 1.42 |
|  |  |  | 18.58** |  | 1.42*** |
| 28 | Pro—Trp—Gly—NH$_2$ | 5 | 19.34 | 0.0956 | 2.02 |
|  |  | 4 | 17.42 | 0.1218 | 0.64 |
|  |  | 3 | 14.75 | 0.1570 | 0.85 |
|  |  |  | 17.17** |  | 1.17*** |
| 29 | Pro—Arg—Gly—Trp—NH$_2$ (SEQ ID NO: 7) | 4 | 18.5 | 0.0529 | 0.91 |
|  |  |  | 18.5** |  | 0.91*** |
| 30 | Pro—D—Arg—Gly—Trp—NH$_2$ | 4 | 19.33 | 0.0754 | 0.86 |
|  |  |  | 19.33** |  | 0.86*** |
| 31 | 4-OH—Pro—Ile—Gly—Trp—NH$_2$ (SEQ ID NO: 2) | 4 | 12.16 | 0.0732 | 0.87 |
|  |  |  | 12.16** |  | 0.87*** |
| 32 | Pro—Leu—Gly—NH$_2$ | 9 | 29.25 | 0.0041* | 2.20 |
|  |  | 5 | 10.08 | 0.1618 | 0.56 |
|  |  | 4 | 13.92 | 0.0716 | 0.78 |
|  |  | 5 | 17.33 | 0.0815 | 1.82 |
|  |  | 4 | 15.67 | 0.1011 | 0.79 |
|  |  | 6 | 16.16 | 0.0561 | 0.85 |
|  |  | 3 | 1.25 | 0.8735 | 0.07 |
|  |  | 0 | 1.00 | 0.8356 | 0.07 |
|  |  | 1 | 9.00 | 0.3794 | 0.30 |
|  |  | 1 | −3.67 | 0.6486 | −0.15 |
|  |  | 2 | 9.17 | 0.3839 | 0.37 |
|  |  | 4 | 16.75 | 0.1553 | 0.56 |
|  |  | 7 | 45.75 | 0.0047* | 1.42 |
|  |  | 2 | 2.00 | 0.7974 | 0.10 |
|  |  | 6 | 22.84 | 0.0337* | 1.19 |
|  |  |  | 13.77** |  | 0.73*** |
| 33 | 4-Thio—Pro—Leu—Gly—NH$_2$ | 3 | 5.00 | 0.6084 | 0.22 |
|  |  |  | 5.00** |  | 0.22*** |
| 34 | Pro—Trp—Gly—Trp—NH$_2$ (SEQ ID NO: 8) | 3 | 7.5 | 0.4767 | 0.37 |
|  |  |  | 7.5** |  | 0.37*** |
| 35 | Trp—Pro—Leu—Gly—NH$_2$ (SEQ ID NO: 17) | 3 | 3.84 | 0.5805 | 0.21 |
|  |  |  | 3.84** |  | 0.21*** |
| 36 | Pro—Leu—Gly—Tyr—NH$_2$ (SEQ ID NO: 6) | 3 | 15.83 | 0.0741 | 0.84 |
|  |  | 0 | −5.5 | 0.5387 | −0.20 |
|  |  | 4 | 8.75 | 0.3790 | 0.54 |
|  |  |  | 6.36** |  | 0.38*** |
| 37 | Tyr—Pro—Leu—Gly—Trp—NH$_2$ (SEQ ID NO: 32) | 2 | 10.58 | 0.3093 | 0.43 |
|  |  |  | 10.58** |  | 0.43*** |
| 38 | Pro—Ile—Gly—NH$_2$ | 2 | 9.42 | 0.1128 | 0.55 |
|  |  |  | 9.42** |  | 0.55*** |
| 39 | Tyr—Tyr—Pro—Leu—Gly—NH$_2$ (SEQ ID NO: 27) | 2 | 5.25 | 0.3621 | 0.35 |
|  |  |  | 5.25** |  | 0.35*** |
| 40 | Phe—Tyr—Pro—Leu—Gly—NH$_2$ (SEQ ID NO: 23) | 1 | 5.58 | 0.6212 | 0.17 |
|  |  |  | 5.58** |  | 0.17*** |
| 41 | Pro—Lys—Gly—NH$_2$ | 1 | 6.25 | 0.3400 | 0.33 |
|  |  |  | 6.25** |  | 0.33*** |
| 42 | Pro—Orn—Tyr—NH$_2$ | 1 | −1.25 | 0.8344 | −0.09 |
|  |  |  | −1.25** |  | −0.09*** |
| 43 | Pro—Trp—Gly | 0 | −4.42 | 0.5718 | −0.18 |
|  |  |  | −4.42** |  | −0.18*** |

Comments:
a. Tests were run on 12 rats per group
b. CGI: Control group inactive
c. Mobile time = seconds struggling
d. Outliers: Mobile time is over 4 standard deviation
e. Number of Responders: Number of rats in the Drug Group with Mobile Time > (Mean plus Standard Deviation of Control Group)
f. Difference between Drug & CGI = (Mobile Time of Drug Group minus Control Mobile Time), in seconds
g. Student's t-Test - statistical procedure to determine significant difference between the means of two indepenedent samples (Drug & CGI)
h. Z-Score = (Mobile Time of Drug Group minus Control Mobile Time)/(Control Standard Deviation)
i. *significant difference for one-tailed t-Test
j. **Average of mean Mobile Time (Drug vs CGI)
k. ***Average of mean Z-Score (Drug vs CGI)

What is claimed is:

1. A tripeptide composition or salt thereof, comprising a general formula (1):

$$R^1\text{-}Pro^1\text{-}AA^1\text{-}NR^2\text{-}CH_2\text{-}R \qquad (1)$$

where $Pro^1$ represents an amino acid selected from the group consisting of Pro and dehydro-Pro; $AA^1$ represents an amino acid selected from the group consisting of Trp, Orn, Lys, Leu, Arg, D-Arg, and Ile; R is selected from the group consisting of a carboxyl group, a hydroxyalkyl group, a carbamyl group and an alkoxycarbonyl group; $R^1$ is selected from the group consisting of a hydrogen atom, a lower alkyl group having 1 to 3 carbon atoms, a halogen atom, a hydroxyl group, a sulphydryl group, an alkylamino group, and a dialkylamino group; and, $R^2$ is selected from the group consisting of a hydrogen atom and a lower alkyl group having 1 to 3 carbon atoms, with the provisos that: where $Pro^1$ is Pro and $AA^1$ is Leu, Ile, Lys, Arg, or Orn, then $R^1$ and $R^2$ cannot both be a hydrogen atom when R is a carbamyl group; where $Pro^1$ is dehydro-Pro and $AA^1$ is Leu, then $R^1$ and $R^2$ cannot both be a hydrogen atom when R is a carbamyl group; where $Pro^1$ is Pro and $AA^1$ is Leu, $R^1$ and $R^2$ cannot both be a hydrogen atom when R is either a carboxyl group or a hydroxyalkyl group; and, where $Pro^1$ is Pro and $AA^1$ is Trp, $R^1$ and $R^2$ cannot be a hydrogen atom when R is a hydroxyalkyl group.

2. The tripeptide of claim 1 which is Pro-D-Arg-Gly-$NH_2$.
3. The tripeptide of claim 1 which is Pro-Trp-Gly-$NH_2$.
4. The tripeptide of claim 1 which is cis- or trans-4-OH-Pro-D-Arg-Gly-$NH_2$.
5. The tripeptide of claim 1 which is cis- or trans-4-OH-Pro-Ile-Gly-$NH_2$.
6. The tripeptide of claim 1 which is cis- or trans-4-OH-Pro-Arg-Gly-$NH_2$.
7. The tripeptide of claim 1 which is cis- or trans-4-OH-Pro-Trp-Gly-$NH_2$.
8. The tripeptide of claim 1 which is cis- or trans-4-thio-Pro-Leu-Gly-$NH_2$.
9. The tripeptide of claim 1 which is Pro-Leu-Sar-$NH_2$.
10. The tripeptide of claim 1 which is Pro-Trp-NHCH$_2$—CO$_2$H.
11. A tripeptide composition or salt thereof, comprising a general formula (2):

$$R^1\text{-Pro}^1\text{-AA}^1\text{-Ala-R} \qquad (2)$$

where $Pro^1$ represents an amino acid selected from the group consisting of Pro and dehydro-Pro; $AA^1$ represents an amino acid selected from the group consisting of Arg and D-Arg; R is selected from the group consisting of a carboxyl group, a hydroxyalkyl group, a carbamyl group, an alkylcarbamyl group, and an alkoxycarbonyl group; and, $R^1$ is selected from the group consisting of a hydrogen atom, a lower alkyl group having 1 to 3 carbon atoms, a halogen atom, a hydroxyl group, a sulphydryl group, an alkylamino group, and a dialkylamino group; with the proviso that where $Pro^1$ is Pro and $AA^1$ is Arg, then $R^1$ cannot be a hydrogen atom when R is a carboxyl group.

12. The tripeptide of claim 11 which is Pro-Arg-Ala-$NH_2$.
13. A tripeptide composition or salt thereof, comprising a general formula (3):

$$R^1\text{-Pro}^1\text{-AA}^1\text{-Tyr-R} \qquad (3)$$

where $Pro^1$ represents an amino acid selected from the group consisting of Pro and dehydro-Pro; $AA^1$ represents an amino acid of Orn; R is selected from the group consisting of a carboxyl group, a hydroxyalkyl group, a carbamyl group, an alkyl carbamyl group, and an alkoxycarbonyl group; and, $R^1$ is selected from the group consisting of a hydrogen atom, a lower alkyl group having 1 to 3 carbon atoms, a halogen atom, a hydroxyl group, a sulphydryl group, an alkylamino group, and a dialkylamino group.

14. A tetrapeptide composition or salt thereof, comprising a general formula (4):

$$R^1\text{-Pro}^1\text{-AA}^1\text{-Gly-AA}^2\text{-R} \qquad (4)$$

where $Pro^1$ represents an amino acid selected from the group consisting of Pro and dehydro-Pro; $AA^1$ represents an amino acid selected from the group consisting of Ile, Leu, Arg, D-Arg and Trp; $AA^2$ represents an amino acid selected from the group consisting of Trp and Tyr; R is selected from the group consisting of a carboxyl group, hydroxyalkyl group, a carbamyl group, an alkylcarbamyl group, and an alkoxycarbonyl group; and, $R^1$ is selected from the group consisting of a hydrogen atom, a lower alkyl group having 1 to 3 carbon atoms, a halogen atom, a hydroxyl group, a sulphydryl group, an alkylamino group, and a dialkylamino group.

15. The tetrapeptide of claim 14 which is 3,4-dehydro-Pro-D-Arg-Gly-Trp-$NH_2$.
16. The tetrapeptide of claim 14 which is cis- or trans-4-OH-Pro-D-Arg-Gly-Trp-$NH_2$.
17. The tetrapeptide of claim 14 which is cis- or trans-4-OH-Pro-Leu-Gly-Trp-$NH_2$ (SEQ ID NO: 1).
18. The tetrapeptide of claim 14 which is cis- or trans-4-OH-Pro-Ile-Gly-Trp-$NH_2$ (SEQ ID NO: 2).
19. The tetrapeptide of claim 14 which is Pro-Ile-Gly-Trp-$NH_2$ (SEQ ID NO: 3).
20. The tetrapeptide of claim 14 which is Pro-Leu-Gly-Trp-$NH_2$ (SEQ ID NO: 5).
21. The tetrapeptide of claim 14 which is Pro-Arg-Gly-Trp-$NH_2$ (SEQ ID NO: 7).
22. The tetrapeptide of claim 14 which is Pro-D-Arg-Gly-Trp-$NH_2$.
23. The tetrapeptide of claim 14 which is Pro-Trp-Gly-Trp-$NH_2$ (SEQ ID NO: 8).
24. The tetrapeptide of claim 14 which is Pro-Leu-Gly-Tyr-$NH_2$ (SEQ ID NO: 6).
25. A tetrapeptide composition or salt thereof, comprising a general formula (5):

$$R^1\text{-AA}^1\text{-R}^2\text{-Pro}^1\text{-AA}^2\text{Gly-R} \qquad (5)$$

where $Pro^1$ represents an amino acid selected from the group consisting of Pro and dehydro-Pro; $AA^1$ represents an amino acid selected from the group consisting of Trp, Tyr and Phe; $AA^2$ represents an amino acid selected from the group consisting of Leu, Ile and Trp; R is selected from the group consisting of a carboxyl group, hydroxyalkyl group, a carbamyl group, an alkylcarbamyl group, and an alkoxycarbonyl group; and, $R^1$ and $R^2$ each independently are selected from the group consisting of a hydrogen atom, a lower alkyl group having 1 to 3 carbon atoms, a halogen atom, a hydroxyl group, a sulphydryl group, an alkylamino group, or a dialkylamino group, with the provisos that: where $Pro^1$ is Pro and R is a carbamyl group, $R^1$ and $R^2$ cannot both be a hydrogen atom when $AA^1$ is Tyr and $AA^2$ is Trp; where $Pro^1$ is Pro, $AA^2$ is Leu and R is a carbamyl group, $R^1$ and $R^2$ cannot both be a hydrogen atom when $AA^1$ is Phe or Tyr; and where $Pro^1$ is Pro and R is a carbamyl group, $R^1$ and $R^2$ cannot be a hydrogen atom when $AA^1$ is Trp and $AA^2$ is Leu.

26. The tetrapeptide of claim 25 which is 4-F-Phe-cis- or trans-4-OH-Pro-Leu-Gly-$NH_2$ (SEQ ID NO: 15).
27. The tetrapeptide of claim 25 which is 4-F-Phe-cis- or trans-4-OH-Pro-Ile-Gly-$NH_2$ (SEQ ID NO: 16).
28. The tetrapeptide of claim 25 which is 4-F-Phe-Pro-Leu-Gly-$NH_2$ (SEQ ID NO: 12).

29. A pentapeptide composition or salt thereof, comprising a general formula (6):

$$R^1\text{-}AA^1\text{-}AA^2\text{-}R^2\text{-}Pro^1\text{-}AA^3\text{-}Gly\text{-}R \quad (6)$$

where $Pro^1$ represents an amino acid selected from the group consisting of Pro and dehydro-Pro; $AA^1$ and $AA^2$ each independently represent an amino acid selected from the group consisting of Phe and Tyr; $AA^3$ represents an amino acid selected from the group consisting of Leu and Ile; R is selected from the group consisting of a carboxyl group, hydroxyalkyl group, a carbamyl group, an alkylcarbamyl group, and an alkoxycarbonyl group; and, $R^1$ and $R^2$ are each independently selected from the group consisting of a hydrogen atom, a lower alkyl group having 1 to 3 carbon atoms, a halogen atom, a hydroxyl group, a sulphydryl group, an alkylamino group, and a dialkylamino group.

30. The pentapeptide of claim 29 which is Tyr-Tyr-Pro-Leu-Gly-NH$_2$ (SEQ ID NO: 27).

31. The pentapeptide of claim 29 which is Phe-Tyr-Pro-Leu-Gly-NH$_2$ (SEQ ID NO: 23).

32. A pentapeptide composition or salt thereof, comprising a general formula (7):

$$R^1\text{-}AA^1\text{-}R^2\text{-}Pro^1\text{-}AA^2\text{-}Gly\text{-}AA^3\text{-}R \quad (7)$$

where $Pro^1$ represents an amino acid selected from the group consisting of Pro and dehydro-Pro; $AA^1$ represents an amino acid selected from the group consisting of Phe and Tyr; $AA^2$ represents an amino acid selected from the group consisting of Leu, Ile, Arg, D-Arg, and Trp; $AA^3$ represents an amino acid of Trp; R is selected from the group consisting of a carboxyl group, hydroxyalkyl group, a carbamyl group, an alkylcarbamyl group, and an alkoxycarbonyl group; and, $R^1$ and $R^2$ are each independently selected from the group consisting of a hydrogen atom, a lower alkyl group having 1 to 3 carbon atoms, a halogen atom, a hydroxyl group, a sulphydryl group, an alkylamino group, and a dialkylamino group.

33. The pentapeptide of claim 32 which is Tyr-Pro-Trp-Gly-Trp-NH$_2$ (SEQ ID NO: 39).

34. The pentapeptide of claim 32 which is Phe-Pro-Leu-Gly-Trp-NH$_2$ (SEQ ID NO: 31).

35. The pentapeptide of claim 32 which is Tyr-Pro-Leu-Gly-Trp-NH$_2$ (SEQ ID NO: 32).

36. A pentapeptide composition or salt thereof, comprising a general formula (8):

$$R^1\text{-}Pro^1\text{-}AA^1\text{-}AA^2\text{-}Gly\text{-}AA^3\text{-}R \quad (8)$$

where $Pro^1$ represents an amino acid selected from the group consisting of Pro and dehydro-Pro; $AA^1$ and $AA^2$ each independently represent an amino acid selected from the group consisting of Leu and Ile; $AA^3$ represents an amino acid of Trp; R is selected from the group consisting of a carboxyl group, a hydroxyalkyl group, a carbamyl group, an alkylcarbamyl group, and an alkoxycarbonyl group; and, $R^1$ is selected from the group consisting of a hydrogen atom, a lower alkyl group having 1 to 3 carbon atoms, a dehydro group, a halogen atom, a hydroxyl group, a sulphydryl group, an alkylamino group, and a dialkylamino group.

37. A method of treating depression in a patient, comprising the step of administering a peptide or peptides of formula (2) to formula (8) as recited in the appended claims, capable of traversing the blood-brain barrier in a pharmaceutically effective amount so as to impart a therapeutic effect on said patient, with the proviso excluding Trp-Pro-Leu-Gly-NH$_2$.

38. The method of claim 37 wherein said peptide is 4-F-Phe-cis or trans-4-OH-Pro-Ile-Gly-NH$_2$ (SEQ ID NO: 16).

39. The method of claim 37 wherein said peptide is Pro-Leu-Gly-Trp-NH$_2$ (SEQ ID NO: 5).

40. The method of claim 37 wherein said peptide is 4-F-Phe-cis or trans-4-OH-Pro-Leu-Gly-NH$_2$ (SEQ ID NO: 15).

41. The method of claim 37 wherein said peptide is 3,4-Dehydro-Pro-D-Arg-Gly-NH$_2$.

42. The method of claim 37 wherein said peptide is 4-OH-Pro-D-Arg-Gly-Trp-NH$_2$.

43. The method of claim 37 wherein said peptide is cis- or trans-4-OH-Pro-Ile-Gly-NH$_2$.

44. The method of claim 37 wherein said peptide is 4-OH-Pro-D-Arg-Gly-NH$_2$.

45. The method of claim 37 wherein said peptide is 4-F-Phe-Pro-Leu-Gly-NH$_2$ (SEQ ID NO: 12).

46. The pentapeptide of claim 32 which is Tyr-Pro-Trp-Gly-Trp-NH$_2$ (SEQ ID NO: 39).

47. The pentapeptide of claim 32 which is 4-F-Phe-cis- or trans-4-OH-Pro-Ile-Gly-Trp-NH$_2$ (SEQ ID NO: 41).

48. The pentapeptide of claim 32 which is 4-F-Phe-cis- or trans-4-OH-Pro-Leu-Gly-Trp-NH$_2$ (SEQ ID NO: 42).

49. The pentapeptide of claim 32 which is 4-F-Phe-cis- or trans-4-OH-Pro-Arg-Gly-Trp-NH$_2$ (SEQ ID NO:43).

50. A hexapeptide or salt thereof which is 4-F-Phe-cis- or trans-4-OH-Pro-Ile-Gly-Trp-Gly-NH$_2$ (SEQ ID NO: 46).

51. A heptapeptide or salt thereof which is 4-F-Phe-cis- or trans-4-OH-Pro-Ile-Gly-Trp-Gly-Trp-NH$_2$ (SEQ ID NO: 47).

52. A hexapeptide or salt thereof which is 4-F-Phe-cis- or trans-4-OH-Pro-Leu-Gly-Trp-Gly-NH$_2$ (SEQ ID NO: 48).

53. A heptapeptide or salt thereof which is 4-F-Phe-cis- or trans-4-OH-Pro-Leu-Gly-Trp-Gly-Trp-NH$_2$ (SEQ ID NO: 49).

54. A heptapeptide or salt thereof which is Pro-Ile-Gly-Trp-Pro-Ile-Gly-NH$_2$ (SEQ ID NO: 50).

55. A hexapeptide or salt thereof which is 4-F-Phe-cis- or trans-4-OH-Pro-Arg-Gly-Trp-Gly-NH$_2$ (SEQ ID NO: 51).

56. A heptapeptide or salt thereof which is 4-F-Phe-cis- or trans-4-OH-Pro-Arg-Gly-Trp-Gly-Trp-NH$_2$ (SEQ ID NO: 52).

57. A hexapeptide or salt thereof which is 4-OH-Pro-Ile-Gly-4-OH-Pro-Ile-Gly-NH$_2$ (SEQ ID NO: 53).

58. A hexapeptide or salt thereof which is 3,4-dehydro-Pro-D-Arg-Gly-3,4-dehydro-Pro-D-Arg-Gly-NH$_2$.

59. A hexapeptide or salt thereof which is 3,4-dehydro-Pro-D-Arg-Gly-Trp-Gly-Trp-NH$_2$.

60. A pentapeptide which is 3,4-dehydro-Pro-D-Arg-Gly-Trp-Gly-NH$_2$.

61. The method of claim 37 wherein said peptide is Tyr-Pro-Trp-Gly-Trp-NH$_2$ (SEQ ID NO: 39).

62. The method of claim 37 wherein said peptide is Tyr-cis- or trans-4-OH-Pro-Trp-Gly-Trp-NH$_2$ (SEQ ID NO: 40).

63. The method of claim 37 wherein said peptide is 4-F-Phe-cis- or trans-4-OH-Pro-Ile-Gly-Trp-NH$_2$ (SEQ ID NO: 41).

64. The method of claim 37 wherein said peptide is Phe-cis- or trans-4-OH-Pro-Leu-Gly-Trp-NH$_2$ (SEQ ID NO: 42).

65. The method of claim 37 wherein said peptide is 4-F-Phe-cis- or trans-4-OH-Pro-Arg-Gly-Trp-NH$_2$ (SEQ ID NO: 43).

66. The method of claim 37 wherein said peptide is 4-F-Phe-cis- or trans-4-OH-Pro-D-Arg-Gly-Trp-$NH_2$.

67. A method of treating depression in a patient, comprising the step of administering a peptide or peptides of claim 1 capable of traversing the blood-brain barrier in a pharmaceutically effective amount so as to impart a therapeutic effect on said patient.

68. A method of treating depression in a patient, comprising the step of administering the peptide Pro-Ile-Gly-$NH_2$ capable of traversing the blood-brain barrier in a pharmaceutically effective amount so as to impart a therapeutic effect on said patient.

* * * * *

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4Hyp
            / note="Amino acid #1 is either cis- or trans- 4Hyp"

( i x ) FEATURE:
        ( A ) NAME/KEY: Modified-site
        ( B ) LOCATION: 4
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:1:

Xaa   Leu   Gly   Xaa
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4Hyp
            / note="Amino acid #1 is either cis- or trans- 4Hyp."

( i x ) FEATURE:
        ( A ) NAME/KEY: Modified-site
        ( B ) LOCATION: 4
        ( D ) OTHER INFORMATION: /label=Trp-NH2
            / note="Amino acid #4 is a modified Trp residue:
            an amine group replaces a hydroxyl group at the carboxy
            terminus."

( x i ) SEQUENCE DESCRIPTION: SEQ ID NO:2:

Xaa   Ile   Gly   Xaa
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1

(D) OTHER INFORMATION: /label=Trp-NH2
/ note="A modified Trp residue: an amine group
replaces a hydroxyl group at the carboxy terminus."

(xi) SEQUENCE DESCRIPTION: SEQ ID NO:3:

Pro Ile Gly Xaa
1

(2) INFORMATION FOR SEQ ID NO:4:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=3- 4DeH-Pro
/ note="Proline residue with a C3=C4 double bond."

(ix) FEATURE:
(A) NAME/KEY: Modified-site
(B) LOCATION: 4
(D) OTHER INFORMATION: /label=Trp-NH2
/ note="A modified Trp residue: an amide group
replaces a hydroxyl group at the carboxy terminus."

(xi) SEQUENCE DESCRIPTION: SEQ ID NO:4:

Xaa Ile Gly Xaa
1

(2) INFORMATION FOR SEQ ID NO:5:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 4
(D) OTHER INFORMATION: /label=Trp-NH2
/ note="A modified Trp residue: an amine group
replaces a hydroxyl group at the carboxy terminus."

(xi) SEQUENCE DESCRIPTION: SEQ ID NO:5:

Pro Leu Gly Xaa
1

(2) INFORMATION FOR SEQ ID NO:6:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 4
(D) OTHER INFORMATION: /label=Tyr-NH2
/ note="A modified Tyr residue: an amine group
replaces a hydroxyl group at the carboxy terminus."

(xi) SEQUENCE DESCRIPTION: SEQ ID NO:6:

```
        Pro  Leu  Gly  Xaa
        1
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:7:

```
        Pro  Arg  Gly  Xaa
        1
```

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:8:

```
        Pro  Trp  Gly  Xaa
        1
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Tyr-NH2
            / note="A modified Tyr residue: an amine group
            replaces a hyrdoxyl group at the carboxy terminus."

( x i ) SEQUENCE DESCRIPTION: SEQ ID NO:9:

```
        Pro  Ile  Gly  Xaa
        1
```

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /label=Gly-NH2
        / note="A modified Gly residue: an amine group
        replaces a hyrdoxyl group at the carboxy terminus."

( x i ) SEQUENCE DESCRIPTION: SEQ ID NO:10:

Trp Pro Leu Xaa
1

( 2 ) INFORMATION FOR SEQ ID NO:11:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /label=Gly-NH2
        / note="A modified Gly residue: an amine group
        replaces a hydroxyl group at the carboxy terminus."

( x i ) SEQUENCE DESCRIPTION: SEQ ID NO:11:

Phe Pro Leu Xaa
1

( 2 ) INFORMATION FOR SEQ ID NO:12:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=4F- Phe
        / note="Phe residue modified at C4 with a fluorine atom."

( i x ) FEATURE:
    ( A ) NAME/KEY: Modified-site
    ( B ) LOCATION: 4
    ( D ) OTHER INFORMATION: /label=Gly-NH2
        / note="A modified Gly residue: an amine group
        replaces a hydroxyl group at the carboxy terminus."

( x i ) SEQUENCE DESCRIPTION: SEQ ID NO:12:

Xaa Pro Leu Xaa
1

( 2 ) INFORMATION FOR SEQ ID NO:13:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i x ) FEATURE:

( A ) NAME/KEY: Modified-site
( B ) LOCATION: 1
( D ) OTHER INFORMATION: /label=4Cl-Phe
/ note="Phe residue modified at C4 with a chlorine atom."

( i x ) FEATURE:
( A ) NAME/KEY: Modified-site
( B ) LOCATION: 4
( D ) OTHER INFORMATION: /label=Gly-NH2
/ note="A modified Gly residue: an amine group replaces a hydroxyl group at the carboxy terminus."

( x i ) SEQUENCE DESCRIPTION: SEQ ID NO:13:

Xaa Pro Leu Xaa
1

( 2 ) INFORMATION FOR SEQ ID NO:14:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=4F- Phe
/ note="Phe residue modified at C4 with a fluorine atom"

( i x ) FEATURE:
( A ) NAME/KEY: Modified-site
( B ) LOCATION: 4
( D ) OTHER INFORMATION: /label=Gly-NH2
/ note="A modified Gly residue: an amine group replaces a hydroxyl group at the carboxy terminus."

( x i ) SEQUENCE DESCRIPTION: SEQ ID NO:14:

Xaa Pro Ile Xaa
1

( 2 ) INFORMATION FOR SEQ ID NO:15:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=4F- Phe
/ note="Phe residue modified at C4 with a fluorine atom."

( i x ) FEATURE:
( A ) NAME/KEY: Modified-site
( B ) LOCATION: 2
( D ) OTHER INFORMATION: /label=4Hyp
/ note="Amino acid #2 is either cis- or trans- 4Hyp."

( i x ) FEATURE:
( A ) NAME/KEY: Modified-site
( B ) LOCATION: 4
( D ) OTHER INFORMATION: /label=Gly-NH2
/ note="A modified Gly residue: an amine group replaces a hydroxyl group at the carboxy terminus."

( x i ) SEQUENCE DESCRIPTION: SEQ ID NO:15:

Xaa Xaa Leu Xaa
1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4F- Phe
            / note="Phe residue modified at C4 with a fluorine atom."

( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 4
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:16:

Xaa   Xaa   Ile   Xaa
    1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:17:

Trp   Pro   Leu   Xaa
    1

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:18:

Trp   Pro   Ile   Xaa

1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label=4Hyp
            / note="Amino acid #2 is either cis- or trans- 4Hyp."

(ix) FEATURE:
        (A) NAME/KEY: Modified-site
        (B) LOCATION: 4
        (D) OTHER INFORMATION: /label=Gly-NH2
            / note="A modified Gly residue: an amine group
            replaces a hydroxyl group at the carboxy terminus."

(xi) SEQUENCE DESCRIPTION: SEQ ID NO:19:

Trp Xaa Leu Xaa
1

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label=4Hyp
            / note="Amino acid #2 is either cis- or trans- 4Hyp."

(ix) FEATURE:
        (A) NAME/KEY: Modified-site
        (B) LOCATION: 4
        (D) OTHER INFORMATION: /label=Gly-NH2
            / note="A modified Gly residue: an amine group
            replaces a hydroxyl group at the carboxy terminus."

(xi) SEQUENCE DESCRIPTION: SEQ ID NO:20:

Trp Xaa Ile Xaa
1

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=4F- Phe
            / note="Phe modified at C4 with a fluorine atom."

(ix) FEATURE:
        (A) NAME/KEY: Modified-site
        (B) LOCATION: 5

( D ) OTHER INFORMATION: /label=Gly-NH2
/ note="A modified Gly residue: an amine group
replaces a hydroxyl group at the carboxy terminus."

( x i ) SEQUENCE DESCRIPTION: SEQ ID NO:21:

Xaa Tyr Pro Leu Xaa
1             5

( 2 ) INFORMATION FOR SEQ ID NO:22:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=4Cl-Phe
/ note="Phe residue modified at C4 with a chlorine atom."

( i x ) FEATURE:
( A ) NAME/KEY: Modified-site
( B ) LOCATION: 5
( D ) OTHER INFORMATION: /label=Gly-NH2
/ note="A modified Gly residue: an amine group
replaces a hydroxyl group at the carboxy terminus."

( x i ) SEQUENCE DESCRIPTION: SEQ ID NO:22:

Xaa Tyr Pro Leu Xaa
1             5

( 2 ) INFORMATION FOR SEQ ID NO:23:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Gly-NH2
/ note="A modified Gly residue: an amine group
replaces a hydroxyl group at the carboxy terminus."

( x i ) SEQUENCE DESCRIPTION: SEQ ID NO:23:

Phe Tyr Pro Leu Xaa
1             5

( 2 ) INFORMATION FOR SEQ ID NO:24:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Gly-NH2
/ note="A modified Gly residue: an amine group
replaces a hydroxyl group at the carboxy terminus."

( x i ) SEQUENCE DESCRIPTION: SEQ ID NO:24:

```
Phe  Tyr  Pro  Ile  Xaa
 1                    5
```

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=4Hyp
            / note="Amino acid #3 is either cis- or trans- 4Hyp"

( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group replaces a hydroxyl group at the carboxy terminus."

( x i ) SEQUENCE DESCRIPTION: SEQ ID NO:25:

```
Phe  Tyr  Xaa  Leu  Xaa
 1                    5
```

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=4Hyp
            / note="Amino acid #3 is either cis- or trans- 4Hyp."

( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group replaces a hydroxyl group at the carboxy terminus."

( x i ) SEQUENCE DESCRIPTION: SEQ ID NO:26:

```
Phe  Tyr  Xaa  Ile  Xaa
 1                    5
```

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group replaces a hydroxyl group at the carboxy terminus."

( x i ) SEQUENCE DESCRIPTION: SEQ ID NO:27:

Tyr   Tyr   Pro   Leu   Xaa
1                       5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:28:

Tyr   Tyr   Pro   Ile   Xaa
1                       5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=4Hyp
            / note="Amino acid #3 is either cis- or trans- 4Hyp."

( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:29:

Tyr   Tyr   Xaa   Leu   Xaa
1                       5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=4Hyp
            / note="Amino acid #3 is either cis- or trans- 4Hyp."

( i x ) FEATURE:
        ( A ) NAME/KEY: Modified-site
        ( B ) LOCATION: 5
        ( D ) OTHER INFORMATION: /label=Gly-NH2
            / note="A modified Gly residue: an amine group
            replaces a hydroxyl group at the carboxy terminus."

( x i ) SEQUENCE DESCRIPTION: SEQ ID NO:30:

Tyr Tyr Xaa Ile Xaa
1             5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:31:

Phe Pro Leu Gly Xaa
1             5

( 2 ) INFORMATION FOR SEQ ID NO:32:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:32:

Tyr Pro Leu Gly Xaa
1             5

( 2 ) INFORMATION FOR SEQ ID NO:33:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:33:

Phe Xaa Leu Gly Xaa
1             5

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hyrdoxyl group at the carboxy terminus."

( x i ) SEQUENCE DESCRIPTION: SEQ ID NO:34:

Phe  Pro  Ile  Gly  Xaa
1                         5

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:35:

Phe  Xaa  Ile  Gly  Xaa
1                         5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:36:

Tyr  Xaa  Leu  Gly  Xaa (2) INFORMATION FOR SEQ ID NO:37:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /label=Trp-NH2
            / note="A modified Trp residue: an amine group replaces a hydroxyl group at the carboxy terminus."

(xi) SEQUENCE DESCRIPTION: SEQ ID NO:37:

Tyr Pro Ile Gly Xaa
1               5

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /label=4Hyp
            / note="Amino acid #2 is either cis- or trans- 4Hyp."

(ix) FEATURE:
        (A) NAME/KEY: Modified-site
        (B) LOCATION: 5
        (D) OTHER INFORMATION: /label=Trp-NH2
            / note="A modified Trp residue: an amine group replaces a hydroxyl group at the carboxy terminus."

(xi) SEQUENCE DESCRIPTION: SEQ ID NO:38:

Tyr Xaa Leu Gly Xaa
1               5

(2) INFORMATION FOR SEQ ID NO:39:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /label=Trp-NH2
            / note="A modified Trp residue: an amine group replaces a hydroxyl group at the carboxy terminus."

(xi) SEQUENCE DESCRIPTION: SEQ ID NO:39:

Tyr Pro Trp Gly Xaa
1               5

(2) INFORMATION FOR SEQ ID NO:40:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /label=4Hyp
        / note="Amino Acid #2 is either cis- or trans- 4Hyp"

( i x ) FEATURE:
    ( A ) NAME/KEY: Modified-site
    ( B ) LOCATION: 5
    ( D ) OTHER INFORMATION: /label=Trp-NH2
        / note="A modified Trp residue: an amine group
        replaces a hydroxyl group at the carboxy terminus."

( x i ) SEQUENCE DESCRIPTION: SEQ ID NO:40:

Tyr  Xaa  Trp  Gly  Xaa
 1                    5

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4F- Phe
            / note="Phe residue modified at C4 with a fluorine atom."

( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 5
        ( D ) OTHER INFORMATION: /label=Trp-NH2
            / note="A modified Trp residue: an amine group
            replaces a hydroxyl group at the carboxy terminus."

( x i ) SEQUENCE DESCRIPTION: SEQ ID NO:41:

Xaa  Xaa  Ile  Gly  Xaa
     1                    5

( 2 ) INFORMATION FOR SEQ ID NO:42:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4F- Phe
            / note="Phe residue modified at C4 with a fluorine atom."

( i x ) FEATURE:
        ( A ) NAME/KEY: Modified-site ( B ) LOCATION: 2
( D ) OTHER INFORMATION: /label=4Hyp
/ note="Amino acid #2 is either cis- or trans- 4Hyp"

( i x ) FEATURE:
( A ) NAME/KEY: Modified-site
( B ) LOCATION: 5
( D ) OTHER INFORMATION: /label=Trp-NH2
/ note="A modified Trp residue: an amine group
replaces a hydroxyl group at the carboxy terminus."

( x i ) SEQUENCE DESCRIPTION: SEQ ID NO:42:

Xaa Xaa Leu Gly Xaa
1               5

( 2 ) INFORMATION FOR SEQ ID NO:43:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=4F- Phe
/ note="Phe residue modified at C4 with a fluorine atom."

( i x ) FEATURE:
( A ) NAME/KEY: Modified-site
( B ) LOCATION: 2
( D ) OTHER INFORMATION: /label=4Hyp
/ note="Amino acid #2 is either cis- or trans- 4Hyp."

( i x ) FEATURE:
( A ) NAME/KEY: Modified-site
( B ) LOCATION: 5
( D ) OTHER INFORMATION: /label=Trp-NH2
/ note="A modified Trp residue: an amine group
replaces a hydroxyl group at the carboxy terminus."

( x i ) SEQUENCE DESCRIPTION: SEQ ID NO:43:

Xaa Xaa Arg Gly Xaa
1               5

( 2 ) INFORMATION FOR SEQ ID NO:44:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Trp-NH2
/ note="A modified Trp residue: an amine group
replaces a hydroxyl group at the carboxy terminus."

( x i ) SEQUENCE DESCRIPTION: SEQ ID NO:44:

Pro Ile Leu Gly Xaa
1               5

( 2 ) INFORMATION FOR SEQ ID NO:45:

( i ) SEQUENCE CHARACTERISTICS:
( A ) LENGTH: 5 amino acids
( B ) TYPE: amino acid (C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=4Hyp
/ note="Amino acid #1 is either cis- or trans- 4Hyp."

(ix) FEATURE:
(A) NAME/KEY: Modified-site
(B) LOCATION: 5
(D) OTHER INFORMATION: /label=Trp-NH2
/ note="A modified Trp residue: an amine group replaces a hydroxyl group at the carboxy terminus."

(xi) SEQUENCE DESCRIPTION: SEQ ID NO:45:

Xaa Ile Leu Gly Xaa
1               5

(2) INFORMATION FOR SEQ ID NO:46:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=4F- Phe
/ note="Phe residue modified at C4 with a flourine atom."

(ix) FEATURE:
(A) NAME/KEY: Modified-site
(B) LOCATION: 2
(D) OTHER INFORMATION: /label=4Hyp
/ note="Amino acid #2 is either cis- or trans- 4Hyp."

(ix) FEATURE:
(A) NAME/KEY: Modified-site
(B) LOCATION: 6
(D) OTHER INFORMATION: /label=Gly-NH2
/ note="A modified Gly residue: an amine group replaces a hydroxyl group at the carboxy terminus."

(xi) SEQUENCE DESCRIPTION: SEQ ID NO:46:

Xaa Xaa Ile Gly Trp Xaa
1                   5

(2) INFORMATION FOR SEQ ID NO:47:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1
(D) OTHER INFORMATION: /label=4F- Phe
/ note="Phe residue modified at C4 with a fluorine atom."

(ix) FEATURE:
(A) NAME/KEY: Modified-site
(B) LOCATION: 2
(D) OTHER INFORMATION: /label=4Hyp
/ note="Amino acid #2 is either cis- or trans- 4Hyp."

( i x ) FEATURE:
    ( A ) NAME/KEY: Modified-site
    ( B ) LOCATION: 7
    ( D ) OTHER INFORMATION: /label=Trp-NH2
        / note="A modified Trp residue: an amine group replaces a hydroxyl group at the carboxy terminus."

( x i ) SEQUENCE DESCRIPTION: SEQ ID NO:47:

Xaa Xaa Ile Gly Trp Gly Xaa
1               5

( 2 ) INFORMATION FOR SEQ ID NO:48:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4F- Phe
            / note="Phe residue modified at C4 with a fluorine atom."

( i x ) FEATURE:
        ( A ) NAME/KEY: Peptide
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Peptide
        ( B ) LOCATION: 6
        ( D ) OTHER INFORMATION: /label=Gly-NH2
            / note="A modified Gly residue: an amine group replaces a hydroxyl group at the carboxy terminus."

( x i ) SEQUENCE DESCRIPTION: SEQ ID NO:48:

Xaa Xaa Leu Gly Trp Xaa
1               5

( 2 ) INFORMATION FOR SEQ ID NO:49:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=4F- Phe
            / note="Phe residue modified at C4 with a fluorine atom."

( i x ) FEATURE:
        ( A ) NAME/KEY: Modified-site
        ( B ) LOCATION: 2
        ( D ) OTHER INFORMATION: /label=4Hyp
            / note="Amino acid #2 is either cis- or trans- 4Hyp."

( i x ) FEATURE:
        ( A ) NAME/KEY: Modified-site
        ( B ) LOCATION: 7
        ( D ) OTHER INFORMATION: /label=Trp-NH2
            / note="A modified Trp residue: an amine group replaces a hydroxyl group at the carboxy terminus."

( x i ) SEQUENCE DESCRIPTION: SEQ ID NO:49:

```
Xaa  Xaa  Leu  Gly  Trp  Gly  Xaa
1                 5
```

(2) INFORMATION FOR SEQ ID NO:50:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Gly-NH2
        / note="A modified Gly residue: an amine group replaces a hydroxyl group at the carboxy terminus."

(xi) SEQUENCE DESCRIPTION: SEQ ID NO:50:

```
Pro  Ile  Gly  Trp  Pro  Ile  Xaa
1                 5
```

(2) INFORMATION FOR SEQ ID NO:51:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=4F- Phe
        / note="Phe residue modified at C4 with a fluorine atom."

(ix) FEATURE:
        (A) NAME/KEY: Modified-site
        (B) LOCATION: 2
        (D) OTHER INFORMATION: /label=4Hyp
        / note="Amino acid #2 is either cis- or trans- 4Hyp."

(ix) FEATURE:
        (A) NAME/KEY: Modified-site
        (B) LOCATION: 6
        (D) OTHER INFORMATION: /label=Gly-NH2
        / note="A modified Gly residue: an amine group replaces a hydroxyl group at the carboxy terminus."

(xi) SEQUENCE DESCRIPTION: SEQ ID NO:51:

```
Xaa  Xaa  Arg  Gly  Trp  Xaa
1                 5
```

(2) INFORMATION FOR SEQ ID NO:52:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=4F- Phe
        / note="Phe residue modified at C4 with a fluorine atom."

(ix) FEATURE:
        (A) NAME/KEY: Modified-site (B) LOCATION: 2
(D) OTHER INFORMATION: /label=4Hyp
    / note="Amino acid #2 is either cis- or trans- 4Hyp."

(ix) FEATURE:
    (A) NAME/KEY: Modified-site
    (B) LOCATION: 7
    (D) OTHER INFORMATION: /label=Trp-NH2
        / note="A modified Trp residue: an amine group replaces a hydroxyl group at the carboxy terminus."

(xi) SEQUENCE DESCRIPTION: SEQ ID NO:52:

Xaa Xaa Arg Gly Trp Gly Xaa
1               5

(2) INFORMATION FOR SEQ ID NO:53:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=4Hyp
        / note="Amino acid #1 is either cis- or trans- 4Hyp."

(ix) FEATURE:
    (A) NAME/KEY: Modified-site
    (B) LOCATION: 4
    (D) OTHER INFORMATION: /label=4Hyp
        / note="Amino acid #4 is either cis- or trans- 4Hyp."

(ix) FEATURE:
    (A) NAME/KEY: Modified-site
    (B) LOCATION: 6
    (D) OTHER INFORMATION: /label=Gly-NH2
        / note="A modified Gly residue: an amine group replaces a hydroxyl group at the carboxy terminus."

(xi) SEQUENCE DESCRIPTION: SEQ ID NO:53:

Xaa Ile Gly Xaa Ile Xaa
1               5

(2) INFORMATION FOR SEQ ID NO:54:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 4
    (D) OTHER INFORMATION: /label=Gly-NH2
        / note="A modified Gly residue: an amine group replaces a hyrdoxyl group at the carboxy terminus."

(xi) SEQUENCE DESCRIPTION: SEQ ID NO:54:

Tyr Pro Trp Xaa
1